(12) United States Patent
Lim et al.

(10) Patent No.: US 10,669,313 B2
(45) Date of Patent: Jun. 2, 2020

(54) MULTITARGET-DIRECTED BIO-INORGANIC HYBRID STRUCTURE

(71) Applicant: INDUSTRY-ACADEMIC COOPERATION FOUNDATION, YONSEI UNIVERSITY, Seoul (KR)

(72) Inventors: Yong Beom Lim, Seoul (KR); Woo Jin Jeong, Seoul (KR)

(73) Assignee: INDUSTRY-ACADEMIC COOPERATION FOUNDATION, YONSEI UNIVERSITY, Seoul (KR)

( * ) Notice: Subject to any disclaimer, the term of this patent is extended or adjusted under 35 U.S.C. 154(b) by 0 days.

(21) Appl. No.: 15/820,313

(22) Filed: Nov. 21, 2017

(65) Prior Publication Data

US 2018/0148479 A1 May 31, 2018

(30) Foreign Application Priority Data

Nov. 25, 2016 (KR) .................. 10-2016-0158618
Oct. 24, 2017 (KR) .................. 10-2017-0138666

(51) Int. Cl.

| C07K 7/64 | (2006.01) |
|---|---|
| C07K 7/06 | (2006.01) |
| C07K 7/08 | (2006.01) |
| C07K 17/02 | (2006.01) |
| C07K 14/005 | (2006.01) |
| A61K 38/00 | (2006.01) |

(52) U.S. Cl.
CPC .............. *C07K 7/64* (2013.01); *C07K 7/06* (2013.01); *C07K 7/08* (2013.01); *C07K 14/005* (2013.01); *C07K 17/02* (2013.01); *A61K 38/00* (2013.01); *C07B 2200/11* (2013.01); *C07K 2319/095* (2013.01); *C07K 2319/735* (2013.01); *C12N 2740/16322* (2013.01)

(58) Field of Classification Search
None
See application file for complete search history.

(56) References Cited

U.S. PATENT DOCUMENTS 6,646,113 B1 * 11/2003 Dreyfuss .............. C07K 14/475
435/252.3
2014/0206061 A1 * 7/2014 Linn ..................... C07K 7/08
435/188

FOREIGN PATENT DOCUMENTS

| KR | 10-1581926 B1 | 1/2016 |
|---|---|---|
| WO | 2002/072141 A2 | 9/2002 |
| WO | 2009/105671 A2 | 8/2009 |
| WO | 2010/118169 A2 | 10/2010 |
| WO | 2013/025052 A2 | 2/2013 |

OTHER PUBLICATIONS

Office Action in corresponding Korean patent application No. 10-2017-0138666 dated Jun. 1, 2019.
Backer, M.V., et al., Bioconjugate Chem., 2002, 13 (3), pp. 462-467.

* cited by examiner

*Primary Examiner* — Maury A Audet
(74) *Attorney, Agent, or Firm* — Novick, Kim & Lee, PLLC; Jae Youn Kim

(57) ABSTRACT

Provided herein is a multitarget-directed bio-inorganic hybrid structure. The hybrid structure is based on carbon nanotubes, and includes: carbon nanotubes; and two or more peptides bound to a surface of the carbon nanotubes and each independently interacting with different target molecules.

2 Claims, 17 Drawing Sheets
(16 of 17 Drawing Sheet(s) Filed in Color)
Specification includes a Sequence Listing.

SEQUENCE LISTING

```
<160> NUMBER OF SEQ ID NOS: 7

<210> SEQ ID NO 1
<211> LENGTH: 14
<212> TYPE: PRT
<213> ORGANISM: Artificial Sequence
<220> FEATURE:
<223> OTHER INFORMATION: ARM

<400> SEQUENCE: 1

Thr Arg Gln Ala Arg Arg Asn Arg Arg Arg Arg Trp Arg Arg
1               5                   10

<210> SEQ ID NO 2
<211> LENGTH: 10
<212> TYPE: PRT
<213> ORGANISM: Artificial Sequence
<220> FEATURE:
<223> OTHER INFORMATION: NES

<400> SEQUENCE: 2

Cys Leu Pro Pro Leu Glu Arg Leu Thr Arg
1               5                   10

<210> SEQ ID NO 3
<211> LENGTH: 12
<212> TYPE: PRT
<213> ORGANISM: Artificial Sequence
<220> FEATURE:
<223> OTHER INFORMATION: cyc-EAK including amino acid

<400> SEQUENCE: 3

Ala Glu Ala Ala Ala Lys Glu Ala Ala Ala Lys Ala
1               5                   10

<210> SEQ ID NO 4
```

```
<211> LENGTH: 8
<212> TYPE: PRT
<213> ORGANISM: Artificial Sequence
<220> FEATURE:
<223> OTHER INFORMATION: self-assembly domain

<400> SEQUENCE: 4

Lys Phe Glu Phe Lys Phe Glu Phe
1               5

<210> SEQ ID NO 5
<211> LENGTH: 9
<212> TYPE: PRT
<213> ORGANISM: Artificial Sequence
<220> FEATURE:
<223> OTHER INFORMATION: self-assembly domain

<400> SEQUENCE: 5

Lys Lys Phe Glu Phe Lys Phe Glu Phe
1               5

<210> SEQ ID NO 6
<211> LENGTH: 26
<212> TYPE: RNA
<213> ORGANISM: Artificial Sequence
<220> FEATURE:
<223> OTHER INFORMATION: forward primer

<400> SEQUENCE: 6
cgagagctcg ctatgttcct tgggtt                                            26

<210> SEQ ID NO 7
<211> LENGTH: 26
<212> TYPE: RNA
<213> ORGANISM: Artificial Sequence
<220> FEATURE:
<223> OTHER INFORMATION: reverse primer

<400> SEQUENCE: 7
cgtggtacca tccctaggag ctgttg                                            26
```

MULTITARGET-DIRECTED BIO-INORGANIC HYBRID STRUCTURE

CROSS-REFERENCE TO RELATED APPLICATION

This application claims priority to and the benefit of Korean Patent Application Nos. 10-2016-0158618 filed on Nov. 25, 2016, and 10-2017-0138666 filed on Oct. 24, 2017, the disclosures of which are incorporated herein by reference in their entirety.

INCORPORATION OF SEQUENCE LISTING

This application contains a sequence listing submitted in Computer Readable Form (CRF). The CFR file containing the sequence listing is entitled "9-PK3921920-SequenceListing.txt", which was created and modified on Nov. 21, 2017, and is 4,096 bytes in size. The information in the sequence listing is incorporated herein by reference in its entirety.

BACKGROUND

1. Field of the Invention

The present disclosure relates to a multitarget-directed bio-inorganic hybrid structure, and more particularly, to a hybrid structure for targeting a heterogeneous target material by using an inorganic material as a scaffold and attaching a heterogeneous inhibitor to a surface of the scaffold.

2. Discussion of Related Art

For the past several years, a wide variety of tumor-specific therapeutic proteins including antibodies, antibody fragments, and ligands for cell surface receptors have been developed and clinically tested. Such therapeutic proteins are conjugated to various kinds of therapeutic toxins such as small molecule drugs, enzymes, radioactive isotopes, protein toxins, and other toxins for specific delivery to a patient.

Among these, RNA-protein complexes have been recognized as new and attractive therapeutic targets for 20 years. However, efforts to develop drugs for RNA targeting have not been fruitful.

One of the main causes of difficulty is that RNA and proteins form complexes and thus are difficult to be used as monomolecular drugs capable of suppressing only a single target. Meanwhile, multitarget-directed ligands (MTDLs) for inhibiting multifactorial complex disease pathways that simultaneously affect pathologically relevant targets such as Alzheimer's diseases, diabetes, cancer, viral diseases, and the like that are incurable with existing single medications have recently been developed.

MTDLs are hybrid ligands obtained by covalently linking active pharmacophores acting on different targets. In particular, recent studies have reported that dual target-directed biospecific antibodies directed against the human immunodeficiency virus type-1 (HIV-1) cell entry process are the most potent and common HIV-neutralizing antibodies to date.

Meanwhile, molecular vehicles for targeted drug delivery were reported in a document [Backer, M. V., et al., Bioconjugate Chem. 13 (2002) 462-467]. WO 2010/118169 discloses a human protein scaffold with controlled serum pharmacokinetics. A method and composition related to peptides and proteins with a C-terminal element crossreferenced to related application is disclosed in WO 2009/105671. In addition, targeted ligands are disclosed in WO 2002/072141.

SUMMARY OF THE INVENTION

Provided is a multitarget-directed ligand (MTDL) capable of simultaneously inhibiting a plurality of biomaterials associated with the occurrence of diseases by covalently linking various drugs to a single molecule, by applying carbon nanotubes as a scaffold.

According to an embodiment of the present disclosure, a hybrid structure includes: carbon nanotubes; and two or more peptides bound to a surface of the carbon nanotubes and each independently interacting with different target molecules.

In one embodiment, the hybrid structure includes: a first self-assembling peptide interacting with a first target molecule; and a second self-assembling peptide interacting with a second target molecule.

In one embodiment, the first target molecule and the second target molecule form a multimolecular complex.

In one embodiment, the first self-assembling peptide and the second self-assembling peptide simultaneously interact with the multimolecular complex.

In one embodiment, the first self-assembling peptide includes an arginine rich motif (ARM), and the second self-assembling peptide includes a nuclear export signal (NES).

In one embodiment, the first self-assembling peptide and the second self-assembling peptide each include a self-assembly domain.

In one embodiment, the ARM has an amino acid sequence of SEQ ID NO: 1 below.

<SEQ ID NO: 1>
TRQARRNRRRRWRR

In one embodiment, the NES has an amino acid sequence of SEQ ID NO: 2 below.

<SEQ ID NO: 2>
CLPPLERLTR

In one embodiment, the self-assembly domain has an amino acid sequence of SEQ ID NO: 4 below.

<SEQ ID NO: 4>
KFEFKFEF

According to another embodiment of the present disclosure, a composition for inhibiting a multimolecular complex includes the hybrid structure.

BRIEF DESCRIPTION OF THE DRAWINGS

The patent or application file contains at least one drawing/photograph executed in color. Copies of this patent or patent application with color drawing(s)/photograph(s) will be provided by the Office upon request and payment of the necessary fee.

These and/or other aspects will become apparent and more readily appreciated from the following description of the embodiments, taken in conjunction with the accompanying drawings in which.

DETAILED DESCRIPTION OF EXEMPLARY EMBODIMENTS

Figure 1:
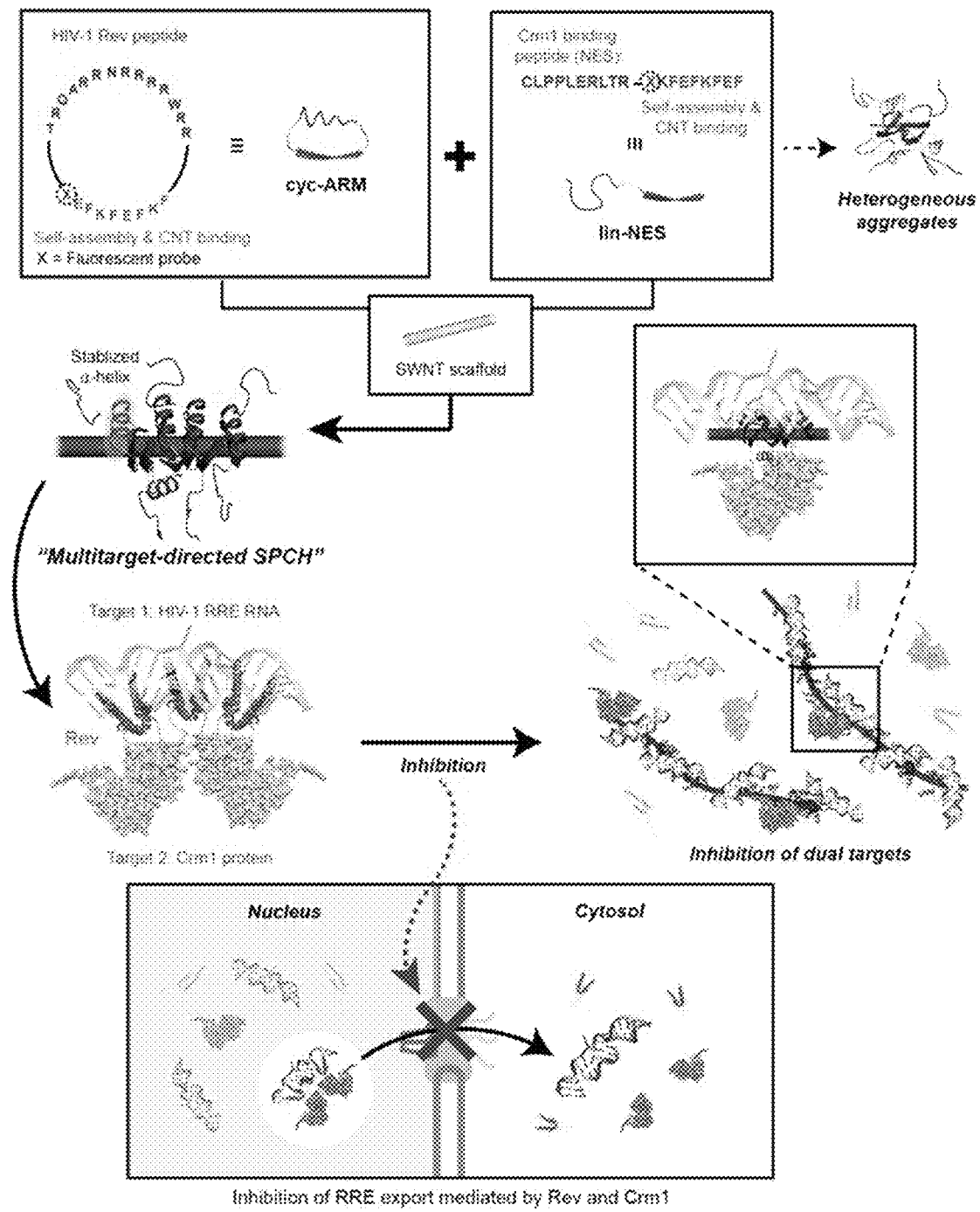
FIG. 1 is a conceptual view of a bio-inorganic hybrid structure according to the present disclosure.
Figure 2:
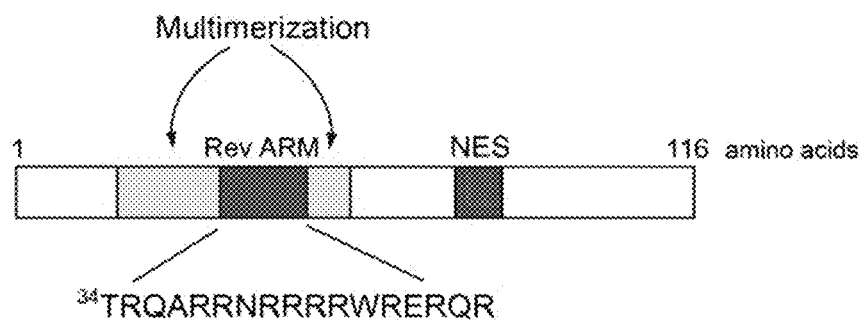
FIG. 2 illustrates a domain structure of a Rev peptide.
Figure 3:
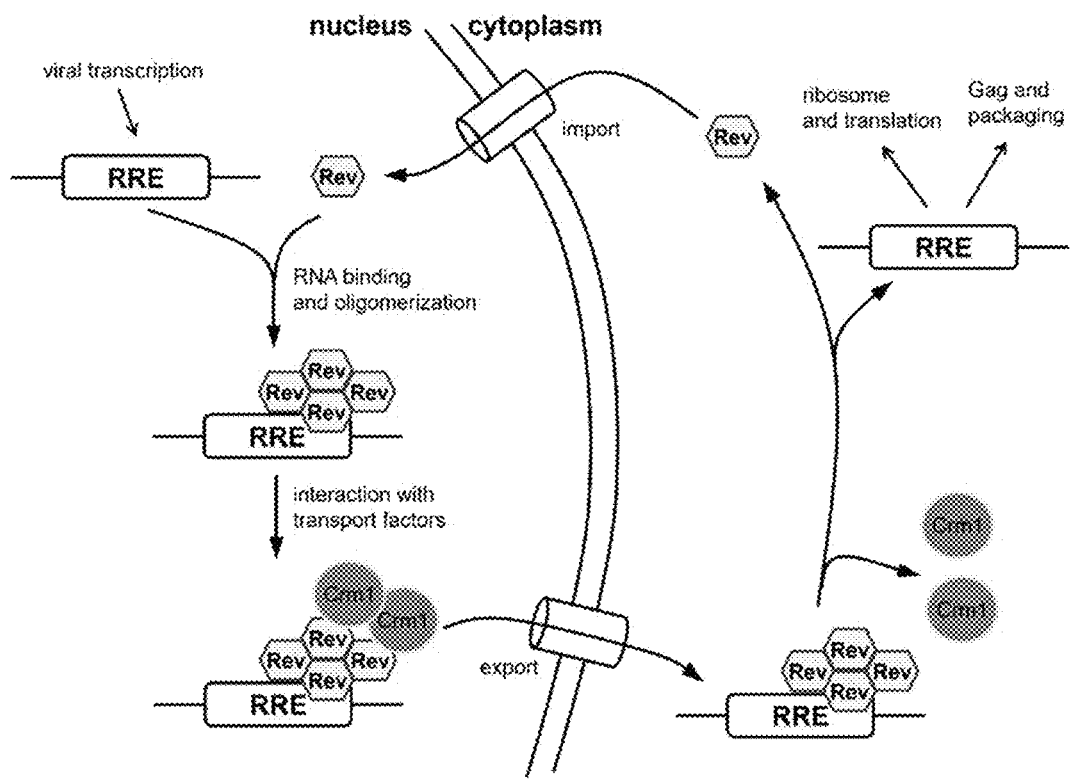
FIG. 3 illustrates a Rev-response element (RRE): Rev: Crm1 complex interaction system for the nucleocytoplasmic export of RRE RNA.
Figure 4:
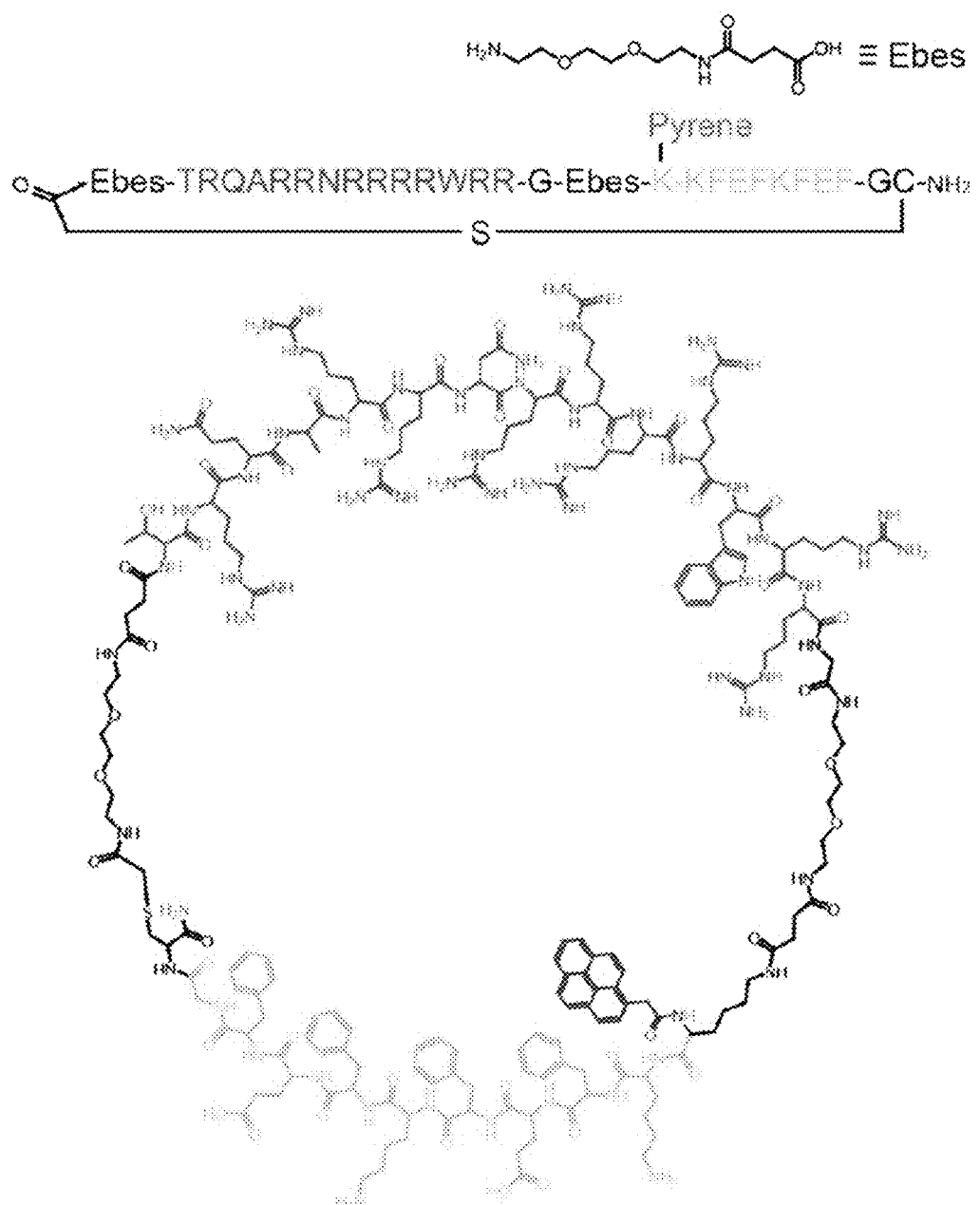
FIG. 4 illustrates an amino acid sequence and structural formula of an arginine-rich motif (ARM) peptide of the present disclosure.
Figure 5:
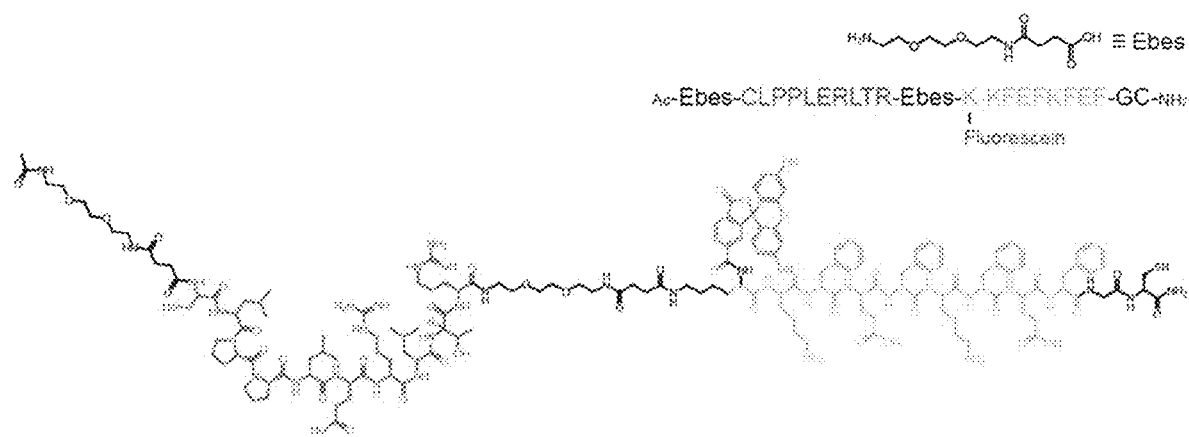
FIG. 5 illustrates an amino acid sequence and structural formula of a nuclear export signal (NES) peptide of the present disclosure.
Figure 6:
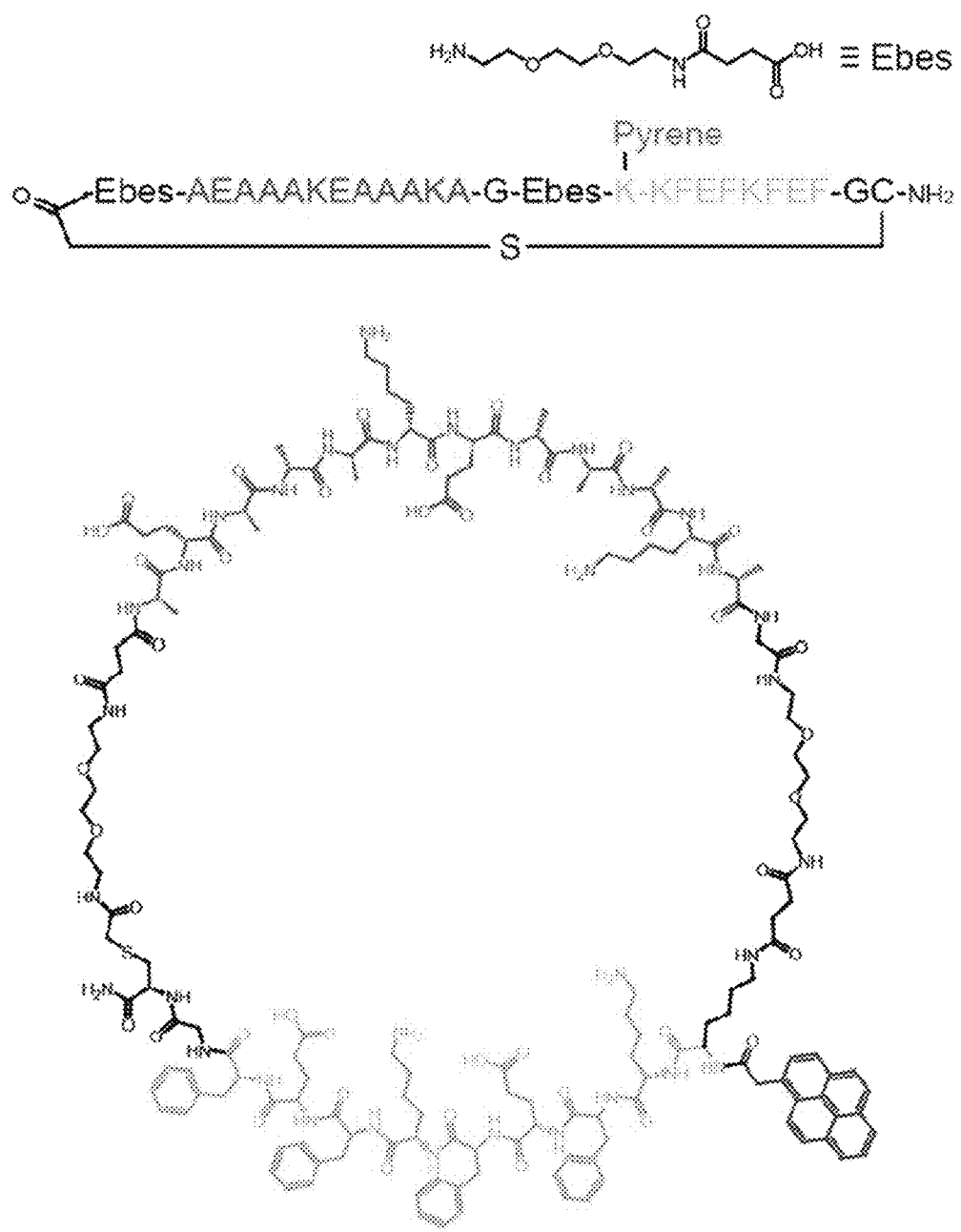
FIG. 6 illustrates an amino acid sequence and structural formula of an erythrocyte adenylate kinase (EAK) peptide of the present disclosure.
Figure 7:
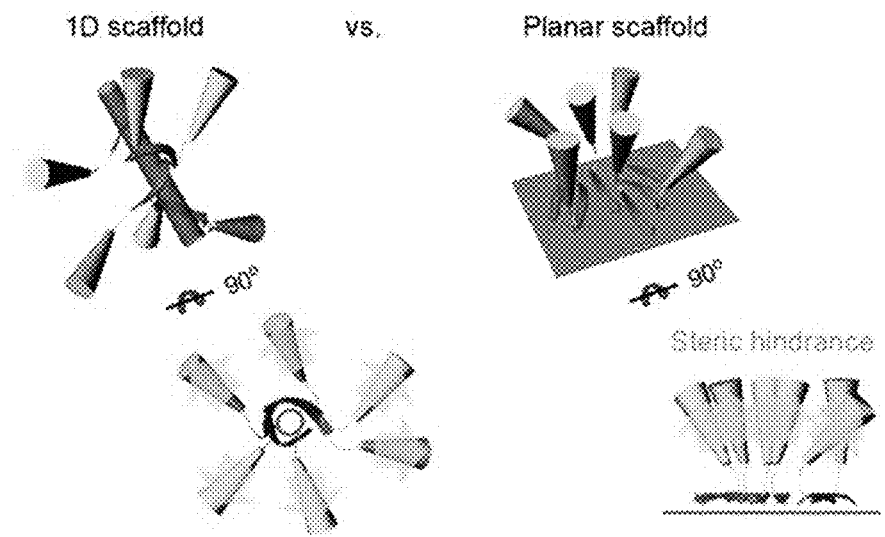
FIG. 7 is a diagram for comparing structural advantages of a carbon nanotube (CNT) scaffold (1D scaffold) with those of a planar scaffold.

Hereinafter, the present disclosure will be described with reference to the accompanying drawings. The present disclosure may, however, be embodied in many different forms, and should not be construed as limited to embodiments set forth herein. In the drawings, parts irrelevant to the description are omitted for clear explanation of the present disclosure, and like reference numerals denote like elements throughout the specification.

When an element is referred to as "comprising" or "including" a component, it does not preclude another component but may further include the other component unless the context clearly indicates otherwise.

Unless otherwise defined, the present disclosure may be carried out by general techniques commonly used in molecular biology, microbiology, protein purification, protein engineering, DNA sequencing, and recombinant DNA fields within the capacity of those of ordinary skill in the art. The techniques are known to those of ordinary skill in the art and are described in numerous standard texts and references.

Unless otherwise defined herein, all technical and scientific terms used herein have the same meaning as commonly understood by one of ordinary skill in the art to which the disclosure pertains.

Although any methods and materials similar or equivalent to those described in the present specification have been found to be used in the practice or testing of the disclosure, some preferred methods and materials are described. The present disclosure is not limited to specific methodologies, protocols, and reagents, as it can be used in various ways depending on the context used by those of ordinary skill in the art.

As used herein, the singular forms include plural objects unless the context clearly indicates otherwise. In addition, unless otherwise indicated, nuclear acids are written left to right in a 5' to 3' orientation, and amino acid sequences are written left to right in an amino to carboxyl orientation. Hereinafter, the present disclosure will be described in more detail.

According to an embodiment of the present disclosure, a hybrid structure includes: carbon nanotubes (CNTs); and two or more peptides bound to a surface of the CNTs and each independently interacting with different target molecules.

In the present disclosure, the concept of multitarget-directed ligands (MTDLs) is applied to supramolecular bio-inorganic nanohybrid systems or hybrid structures.

The CNTs have received much attention as a scaffold of artificial biomacromolecules developed by bio-inorganic hybridization due to a high load capacity of guest materials, biocompatibility, in vivo stability, and cell-penetrating capability.

The CNTs are able to display functional units of biopolymers, such as active protein fractions isolated from proteins, on their surface in a multivalent manner, and thus CNT-based bio-inorganic hybrids have potential as powerful inhibitors of pathogenic biomolecular interactions.

In addition, physical, optical, and electrical characteristics of the CNTs expand the range of applications for hybrid structures to fields that have not been accessible using natural biomolecules.

The peptide refers to a polymer composed of one or more amino acids linked by amide bonds (or peptide bonds).

The general rules for naming the peptides may be based on a three-letter or single-letter amino acid code unless specifically indicated otherwise. For example, the central portion of an amino acid structure is represented by a three-letter code (e.g., Ala or Lys), and may be assumed as being in an L-stereoscopic form unless a D-stereoscopic form (e.g., D-Ala or D-Lys) is specifically indicated by writing "D-" in front of the three-letter code. Amino acid residues constituting the peptide may be natural or non-natural amino acid residues.

Since the hybrid structure includes two or more peptides bound to the surface of the CNTs and each independently interacting with different target molecules, the hybrid structure may simultaneously interact with two or more target molecules.

The term "interaction" as used herein may refer to direct or indirect interaction, and may also mean direct binding or indirect binding, and binding may be mediated via other molecules.

That is, the term "interaction" or "binding" as used herein includes all interaction forms, including direct binding and indirect binding.

FIG. 1 is a conceptual view of a bio-inorganic hybrid structure according to the present disclosure.

Referring to FIG. 1, the hybrid structure is based on CNTs, and may include two or more self-assembling peptides bound to the surface of the CNTs.

The hybrid structure may include: a first self-assembling peptide interacting with a first target molecule; and a second self-assembling peptide interacting with a second target molecule, and the first and second target molecules may form a multimolecular complex.

Thus, the first self-assembling peptide and the second self-assembling peptide may simultaneously interact with the multimolecular complex.

The multimolecular complex may be, for example, an RNA-protein complex, and a variety of in vivo multimolecular complex systems have been studied as a target for drug discovery.

However, previous studies for the development of new drugs have targeted only some of the interfaces of the multimolecular complex or only some of biomolecules, and thus have not achieved an effective inhibitory activity or therapeutic effect.

The inventors of the present disclosure verified that multitarget-directed peptide-CNT hybrids ('SPCHs') can effectively inhibit a multimolecular complex, and the SPCHs may target two interfaces.

The hybrid structure is very suitable for use in inhibiting multimolecular complexes characterized by size and complex molecular interfaces.

For example, single target-directed SPCHs may inhibit a single interface consisting of RNA and a protein only in vitro, whereas multitarget-directed SPCHs may inhibit multimolecular RNA-protein interfaces in vitro and in cells.

The hybrid structure (CNT scaffold) is more effective in multimolecular complexes than in existing approaches using only a single peptide.

The hybrid structure is effective in terms of the following reasons:

(1) Combining the activity of individual ligands may produce a strong synergistic activity; (2) Peptides are very suitable for use in targeting proteins related to biointeractions mediated by spacious and shallow interfaces that cannot be used as drugs due to small molecule inhibitors; (3) A noncovalent hybrid structure may more effectively interact with heterogeneous target biomolecules than existing covalent MTDLs due to advantages in terms of multivalency and adaptability in supramolecular interactions; (4) The length of CNTs is greater than the size of general biomacromolecules, and thus the CNTs may simultaneously interact with many targets; and (5) physical, photonic, and electrical characteristics of CNTs, such as photothermal properties, may effectively immobilize pathogenic biomaterials.

In the present disclosure, a Rev-response element (RRE) RNA: Rev protein: Crm 1 protein interaction system, which is a well-known RNA-protein interaction, is used as a model of multimolecular RNA-protein interactions.

A short α-helical peptide derived from the HIV-1 Rev protein is recognized as a high-affinity site, in particular, in RRE, and the RNA-protein interaction system is well known as a target for drug discovery.

Rev binds the RRE in a multimeric manner, and the RRE-Rev complex may be recognized by Crm1.

Although many attempts have been tried to develop new drugs, previous studies have targeted only the RRE: Rev interface or the RRE-Rev complex: Crm1 interface, which is an interaction interface, and thus none of them have progressed to preclinical development.

The inventors of the present disclosure assembled SPCHs (homo-SPCH) using a single peptide to observe the characteristics of the hybrid structure.

To prepare a peptide with bioactivity and CNT-binding properties, a first self-assembling macrocyclic peptide (cyc-ARM) consisting of the arginine-rich motif (ARM) (14 amino acids) of Rev, a self-assembling and CNT-binding segment labeled with a pyrene fluorophore for intracellular tracking, and their linkers was synthesized.

In particular, the first self-assembling peptide may include an ARM and a self-assembly domain.

The ARM may have an amino acid sequence of SEA ID NO: 1 below, and the self-assembly domain may have an amino acid sequence of SEQ ID NO: 4 below.

<SEQ ID NO: 1>

TRQARRNRRRRWRR

<SEQ ID NO: 4>

KFEFKFEF

The first self-assembling peptide may be represented by Structural Formula 1 below, and may be a cyc-ARM peptide (hereinafter, referred to as 'cyc-ARM'), which is a macrocyclic peptide.

interact with RNA and Crm1 via the ARM and the nuclear export signal (NES), respectively.

Referring to FIGS. 4 and 5, the ARM is a α-helical peptide, and the NES has an irregular stereoscopic structure, and thus the peptide sequences have different structural characteristics.

Thus, the RRE: Rev: Crm1 complex may be a suitable target material for demonstrating the efficacy of the multi-target-directed SPCH including the ARM and the NES as multitarget-directed bioactive ligands.

Referring to FIG. 7, a one-dimensional (1D) structure of the CNTs may provide a significant benefit beyond that of two-dimensional (2D) or three-dimensional (3D) scaffolds having a planar surface.

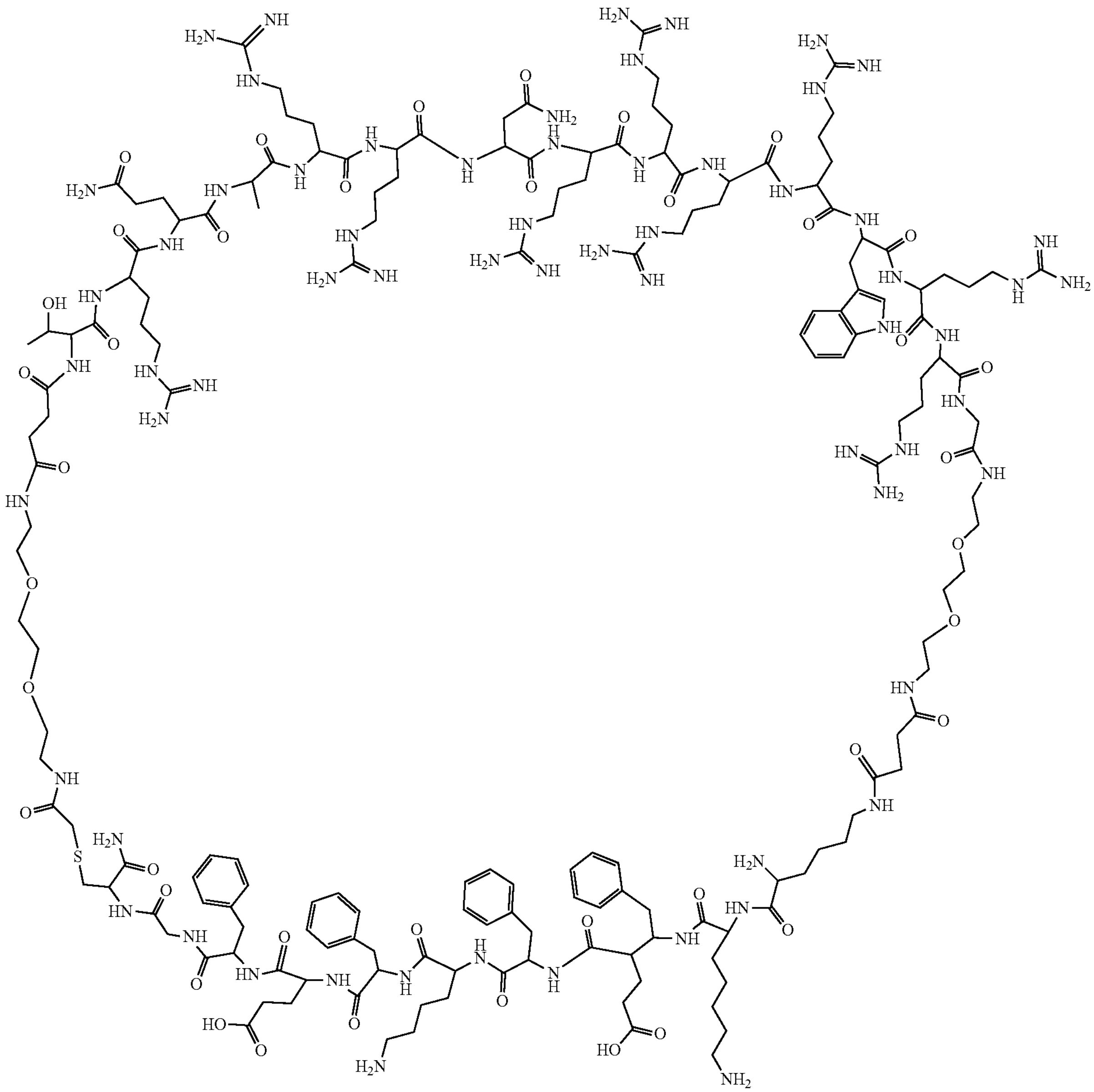 [SMILES: CC1NC(=O)C(CCC(N)=O)NC(=O)C(CCCNC(=N)N)NC(=O)C(C(C)O)NC(=O)CCC(=O)NCCOCCOCCNC(=O)CSCC(C(N)=O)NC(=O)CNC(=O)C(Cc2ccccc2)NC(=O)C(CCC(=O)O)NC(=O)C(Cc2ccccc2)NC(=O)C(CCCCN)NC(=O)C(Cc2ccccc2)NC(=O)C(CCC(=O)O)C(Cc2ccccc2)NC(=O)C(CCCCCN)NC(=O)C(N)CCCCNC(=O)CCC(=O)NCCOCCOCCNC(=O)CNC(=O)C(CCCNC(=N)N)NC(=O)C(CCCNC(=N)N)NC(=O)C(Cc2c[nH]c3ccccc23)NC(=O)C(CCCNC(=N)N)NC(=O)C(CCCNC(=N)N)NC(=O)C(CCCNC(=N)N)NC(=O)C(CCCNC(=N)N)NC(=O)C(CC(N)=O)NC(=O)C(CCCNC(=N)N)NC(=O)C(CCCNC(=N)N)NC1=O]

Referring to FIG. 3, the Rev (see FIG. 2) enables the nucleocytoplasmic translocation or export of unspliced or partially spliced HIV-1 RNA with the aid of Crm1, which is an essential process in viral replication. The Rev may Biomolecular cargo may be exposed to a CNT scaffold without steric hindrance due to a narrow diameter (~1 nm) of single-walled CNTs (SWCNTs). In short bioactive peptides isolated from proteins, it is important to maintain the intrinsic steric conformation closely related to their functionality.

The functionality of CNTs may be achieved by covalent or noncovalent approaches. In a covalent approach, it is not easy to control the orientation and density of functionalized peptides. This is because reactive groups are randomly arranged at fixed positions on the surface of SWCNTs.

In contrast, in a noncovalent approach, specific molecular states of functionalized peptides via supramolecular control may be adjusted. In addition, the noncovalent approach facilitates the preparation of the hybrid structure and the control of a ratio of different types of immobilized cargo. That is, the ratio of different types of cargo immobilized on the hybrid may be in proportion to a concentration ratio of peptides in a solution state.

To prepare the homo-SPCHs, SWCNTs grown by arc-discharging are functionalized with a cyc-ARM in an aqueous sodium chloride (NaCl, 150 mM) solution in a sonication bath to prepare an inorganic-bio hybrid structure (homo-ARM-SPCH) in which the cyc-ARM is bound to the surface of the CNTs.

To quantify the maximum possible amount of the cyc-ARM immobilized on a SWNT sidewall, non-immobilized peptides are isolated from SPCH solutions prepared at various cyc-ARM concentrations by centrifugation, and then the isolated peptides are put into a gel electrophoresis system.

Figure 8:
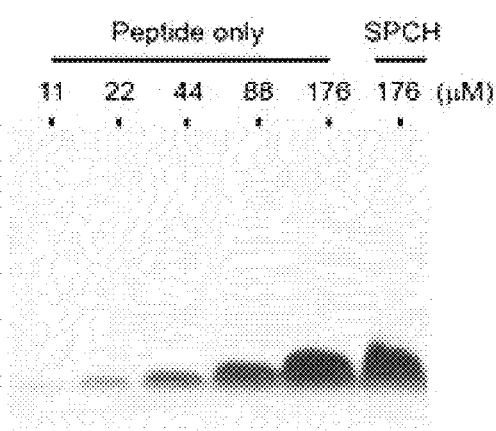
FIG. 8 illustrates sodium dodecyl sulfate (SDS)-polyacrylamide gel electrophoresis (PAGE) analysis results of the amount of an ARM peptide bound to CNTs of the present disclosure (In FIG. 8, values refer to the concentrations of the ARM)
Figure 9:
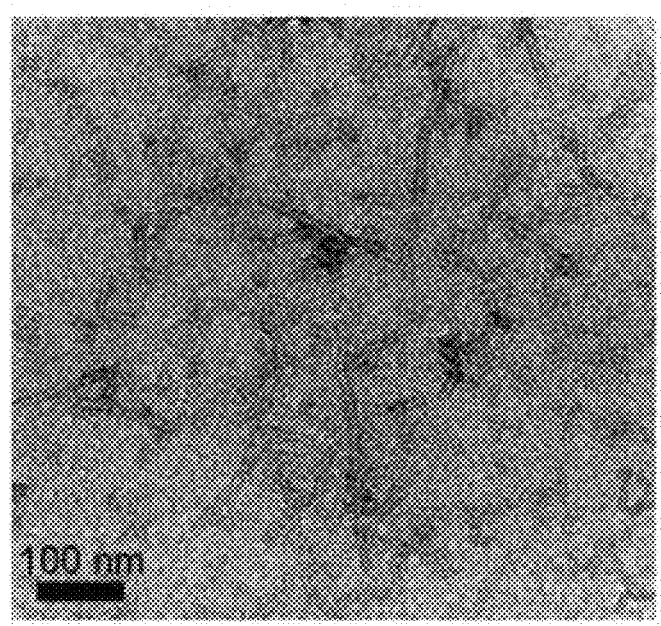
FIG. 9 is a transmission electron microscopy (TEM) image of a bio-inorganic hybrid structure in which an ARM peptide is bound to the surface of CNTs of the present disclosure.

Referring to FIG. 8, through densitometric analysis of electrophoretic bands, it was confirmed that 1.4 nmol of cyc-ARM can bind to 1 μg of SWCNTs. In consideration of the specific surface area of SWCNTs and the calculated surface area of the CNT-binding segment, the coverage of peptides with respect to the surface area of CNTs is ~100%. Under conditions enabling dense coverage of the surface of SWCNTs on which non-immobilized peptides are not present, hydrophobic inorganic scaffolds are effectively degraded and debundled by hybridization as can be seen from the TEM image (see FIG. 9).

A secondary structure of the cyc-ARM immobilized on SWCNTs is observed by CD spectroscopy.

Figure 10:
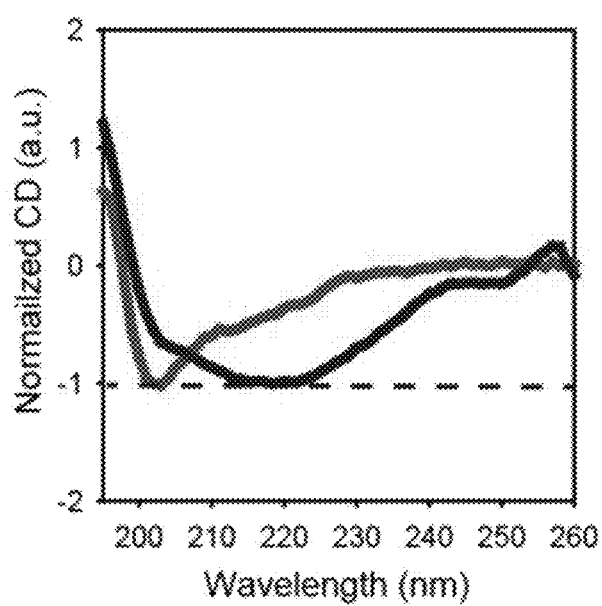
FIG. 10 illustrates circular dichroism (CD) spectra results of an ARM peptide (red) and an ARM-CNT hybrid structure (blue) of the present disclosure.

Referring to FIG. 10, a negative minimum at 222 nm, which is the signal of an α-helical steric conformation, is more intense in a CD spectrum (blue) of the homo-ARM-SPCHC than in a spectrum (red) of the ARM peptide. The enhanced helicity is induced by inorganic scaffold-induced α-helix stabilization. Such stabilization is very important for specific RRE recognition.

Suitability as an inhibitor of in vitro RRE:Rev interactions was evaluated using the hybrid structure. To prepare a stable RRE-Rev complex, first, a complex formation ratio of Rev and RRE (~350 nt) was determined.

RRE (100 nM) and various concentrations of Rev are mixed in HEPES-buffered saline (HBS) and then subjected to an electrophoretic mobility shift assay (EMSA).

Figure 11:
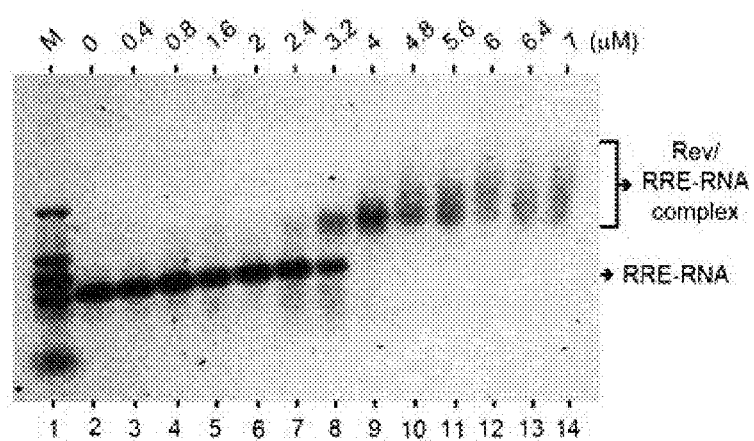
FIG. 11 illustrates electrophoretic mobility shift assay (EMSA) results of an Rev-RRE RNA complex solution of the present disclosure (In FIG. 11, values above the gel refer to the concentration of Rev, and [RRE]=100 nM)

Referring to FIG. 11, since 10-12 Rev molecules can bind to RRE RNA in a multivalent manner, the RRE-Rev complex forms gradually widening electrophoretic bands as the concentration of Rev increases above a critical concentration (see lanes 8 to 14). The wide bands consist of RRE-Rev complexes of many different bound Rev proteins.

Based on the above-described results, a concentration that stably maintains the stable RRE-Rev complex was used in competition experiments (RRE, 100 nM; Rev, 6 μM).

It was confirmed whether Rev in the previously prepared RRE-Rev complexes could be competitively exchanged with the homo-ARM-SPCH.

Figure 12:
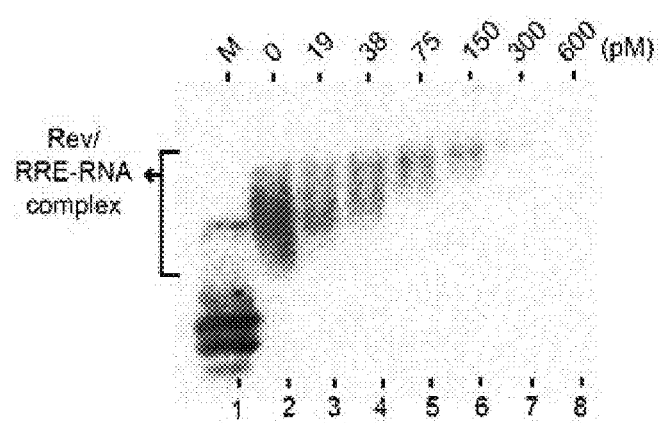
FIG. 12 illustrates EMSA results of an RRE-Rev complex ([RRE]=100 nM, [Rev]=6 µM) according to increase in the concentration of the ARM-CNT hybrid structure of the present disclosure (In FIG. 12, values above the gel refer to the concentration of the ARM-CNT hybrid structure)

Referring to FIG. 12, as the concentration of the homo-ARM-SPCH increases, bands corresponding to the complexes slowly disappear, and this supports a competitive exchange reaction therebetween.

Homo-ARM-SPCHs cannot migrate via a gel, and thus the exchange reaction results in a decrease in the intensity of the bands of the complexes. Considering the fact that the complexes consist of multimeric Rev and huge RNA (~350 nt), competition with hybrids based on small cyc-ARMs is noteworthy.

In addition, lower parts of wide EMSA bands are indicative of Rev-RRE complexes including a smaller number of Revs, and these parts were found to first disappear in the competition experiments. The result coincides with the fact that the complexes including a smaller number of Revs is more susceptible to the exchange reaction.

In addition, the concentrations of Rev and homo-ARM-SPCH under complete exchange conditions were 6 μM and 600 pM, respectively. The result demonstrates that the binding strength of the homo-ARM-SPCH is about 10,000 times greater than that of the Rev protein in RRE binding. Excellent in vitro inhibitory capability of the homo-ARM-SPCH is obtained as a result of the formation of self-assembly hybrids of the homo-ARM-SPCH and due to multivalent characteristics and may be derived from the statistical rebinding mechanism.

Noncovalent interactions are reversible, and thus supramolecular peptide-CNT hybrids (SPCHs) are unstable in cells. Despite the importance of this basic questionable point, intracellular stability of noncovalent peptide-CNT hybrids is not specified at the current level.

To verify the stability, the intracellular behavior of a supramolecular hybrid structure was observed. To distinguish an inorganic scaffold from a pyrene-labeled cyc-ARM, SWCNTs were labeled with rhodamine B.

Figure 13:
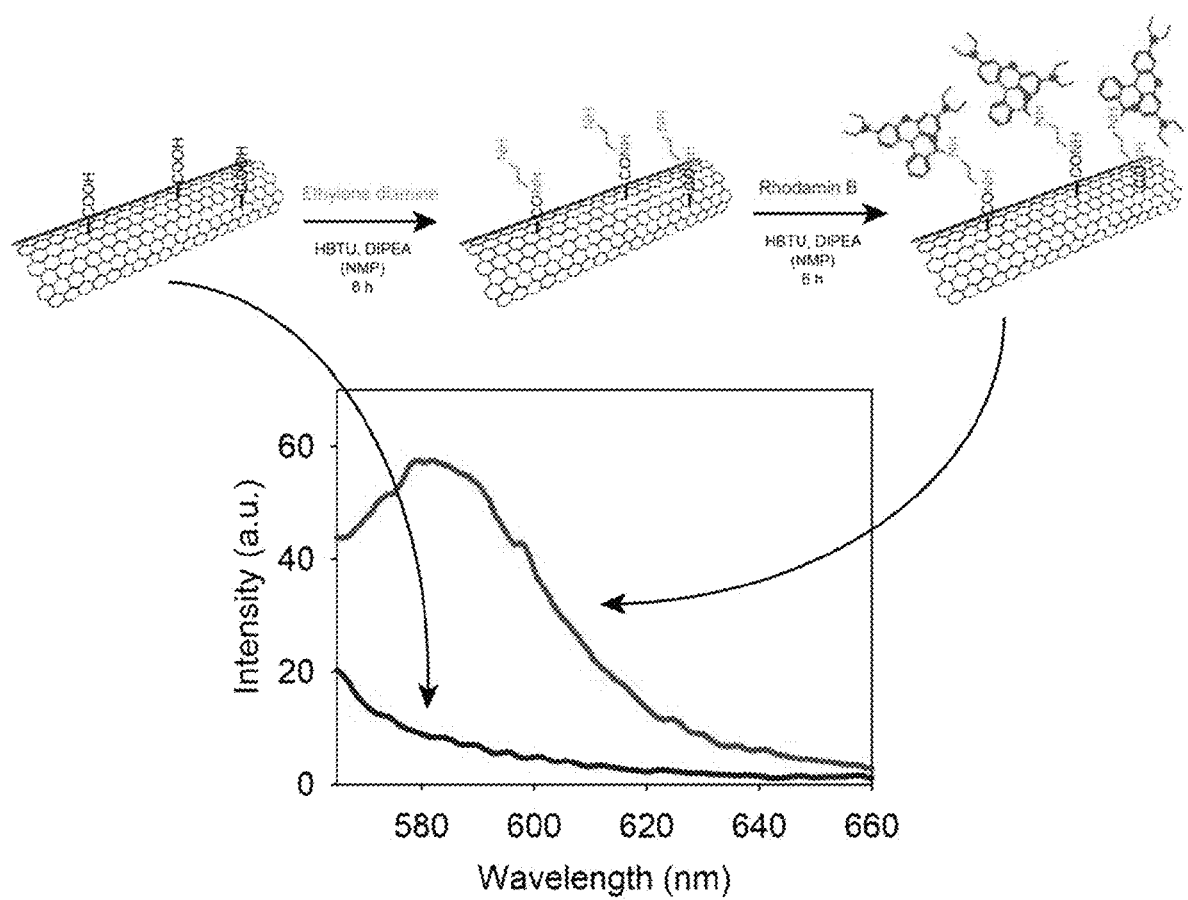
FIG. 13 illustrates fluorescence emission spectra of rhodamine B-labeled single-walled CNTs (SWCNTs) (red) of the present disclosure and rhodamine B-unlabeled SWCNTs (blue)

FIG. 13 illustrates fluorescence emission spectra of rhodamine B-labeled single-walled CNTs (SWCNTs) (red) and rhodamine B-unlabeled SWCNTs (blue).

Referring to FIG. 13, ethylene diamine and rhodamine B were conjugated to a surface of the SWCNTs via the formation of amide bonds using 2-(1H-benzotriazol-1-yl)-1,1,3,3-tetramethyluronium hexalfluorophosphate (HBTU). Fluorescent SWCNTs were functionalized with the peptide and the cyc-ARM via noncovalent binding.

Figure 14:
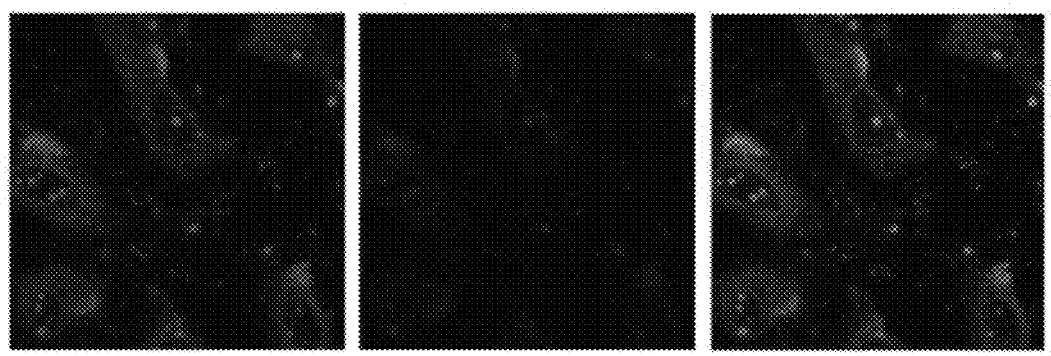
FIG. 14 illustrates images of the intracellular distribution of the ARM-CNT hybrid structure of the present disclosure (red fluorescence (rhodamine B) from SWCNTs (left), blue fluorescence (pyrene) from an ARM peptide (middle), and a merged image showing co-localization of the SWCNTs and the ARM peptide (right)

Referring to FIG. 14, it was confirmed that, after hybrids were cultured for 4 hours, peptides (left image; blue fluorescence) and SWCNTs (middle image; red fluorescence) were widely distributed throughout the entire cell including a nucleus and nucleolus in the nucleus by confocal microscopy. Colocalization of the red fluorescence and the blue fluorescence indicates that the cyc-ARM is not isolated from the SWCNTs in the intracellular environment (left image).

To verify the stability of noncovalent immobilization of the peptides on the SWCNTs in the intracellular environment, cells treated with the cyc-ARM alone or the homo-ARM-SPCH were analyzed by fluorescence recovery after photobleaching (FRAP). The FRAP is a technique used to assess the size-related intracellular mobility of a material by measuring the time needed for fluorescence recovery in a photobleached region.

Figure 15:
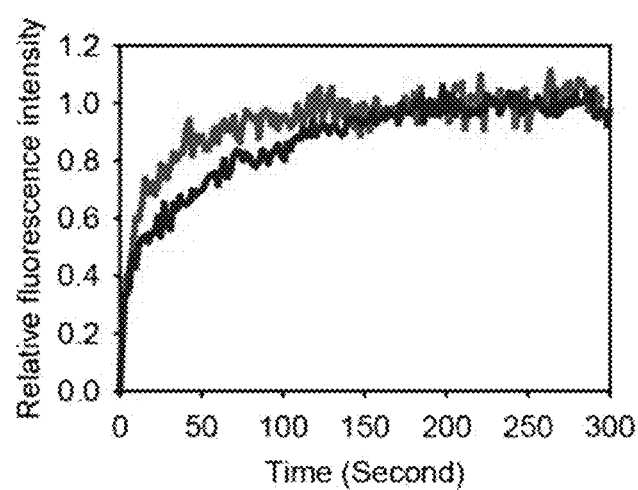
FIG. 15 illustrates quantitative analysis results by fluorescence recovery after photobleaching (FRAP) of the ARM peptide (red) and the ARM-CNT hybrid structure (blue) of the present disclosure.
Figure 16:
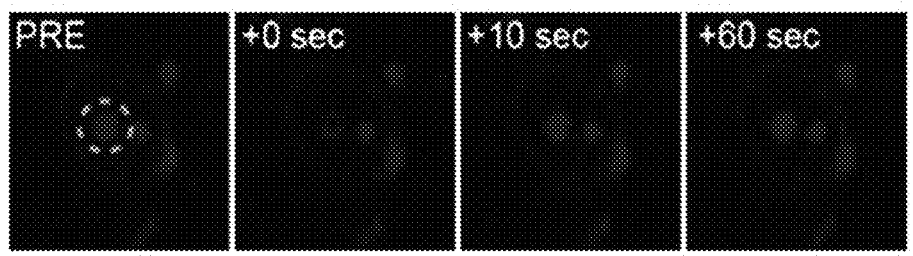
FIG. 16 illustrates FRAP analysis results of the ARM peptide (upper panels) and the ARM-CNT hybrid structure (lower panels) of the present disclosure.
Figure 16:
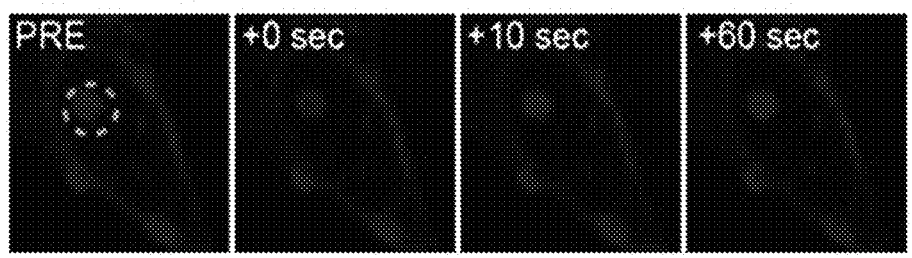

Referring to FIGS. 15 and 16, the fluorescence recovery of the homo-ARM-SPCH was slower than that of the cyc-ARM. The recovery rate is inversely proportional to molecular weight, and thus the results demonstrate that an effective molecular weight of the cyc-ARM may be increased by binding thereof to the SWCNTs. That is, the noncovalent hybrid structure may be maintained intact in cells.

An SWNT hybrid structure including different types of peptides (hetero-SPCHs) was studied using studies on SPCHs including homogeneous ligands. A macrocyclic peptide capable of co-assembling with the cyc-ARM, i.e., cyc-EAK, was synthesized on the SWCNTs.

<SEQ ID NO: 3>
AEAAAKEAAAKA

<SEQ ID NO: 5>
KKFEFKFEF

In particular, the cyc-EAK may be represented by Structural Formula 3 below.

<Structural Formula 3>

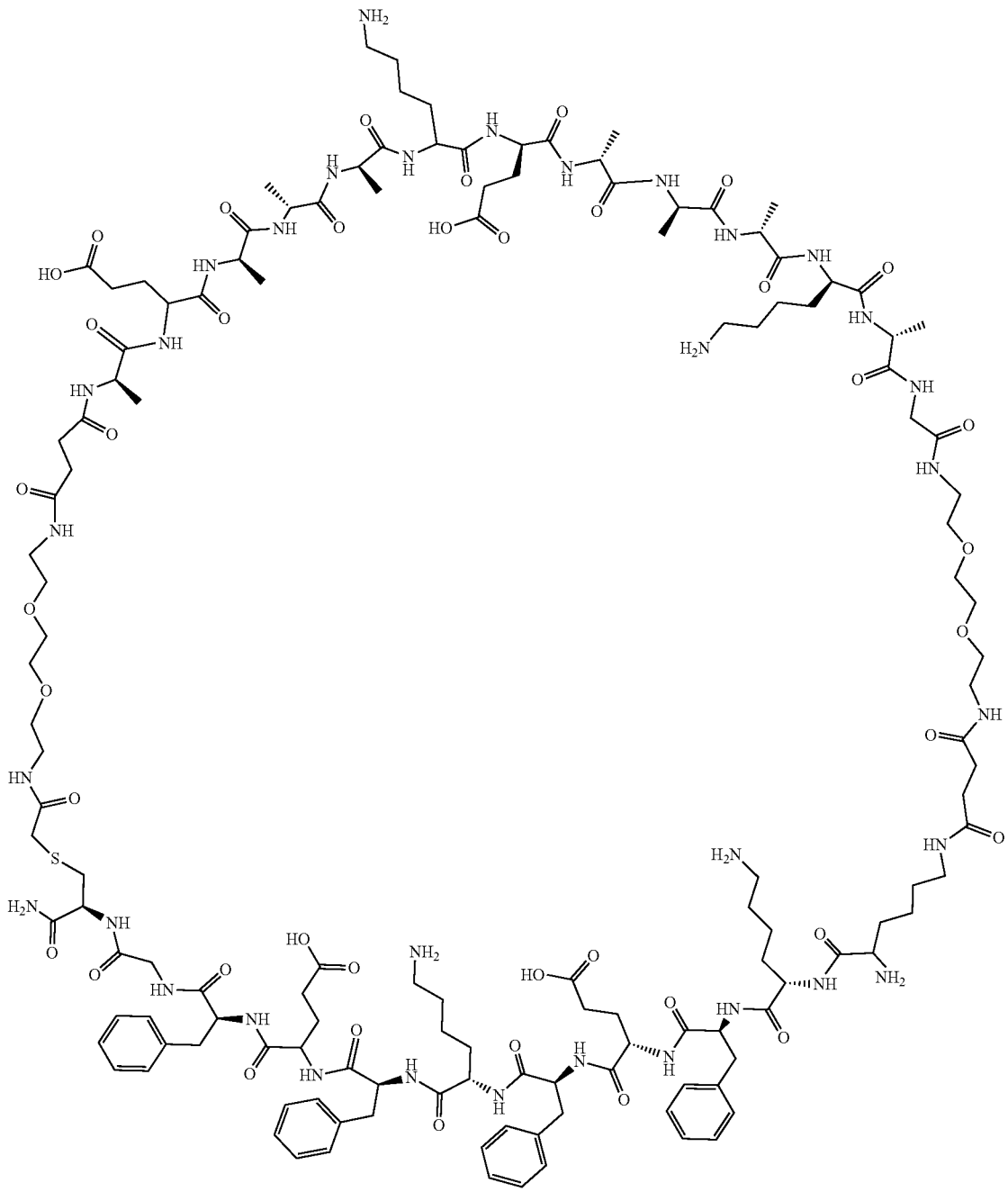

The cyc-EAK may include an amino acid sequence of SEQ ID NO: 3 below, and may further include an amino acid sequence of SEQ ID NO: 5 below.

A Rec α-helix segment of the cyc-ARM may be substituted with an α-helical peptide model (H-AE-AAAKEAAAKA-OH) of cyc-EAK.

In the present disclosure, the cyc-EAK is used as the α-helical peptide model. The peptide has self-assembling properties under conditions in the presence of ions, and thus cyc-ARM and cyc-EAK were dissolved in pure water to prepare a uniform mixture, and a part of the mixture was bound to the SWCNTs, and then ions were injected thereinto.

Figure 17:
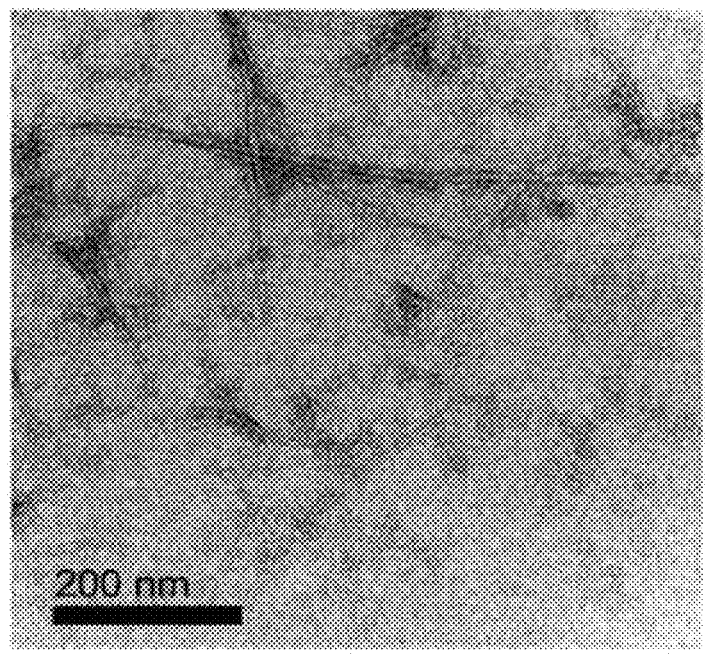
FIG. 17 is a TEM image of a hetero-(A&E)-SPCH of the present disclosure.

Referring to FIG. 17, after being bound to the SWCNTs, ionic force-mediated SWNT functionalization, producing a separate nano-resultant, i.e., hetero-A&E-SPCH, occurred.

Hetero-A&E-SPCH solutions at various cyc-ARM/cyc-EAK ratios were prepared, and inhibitory capability thereof on in vitro RRE:Rev interactions was tested.

Figure 18:
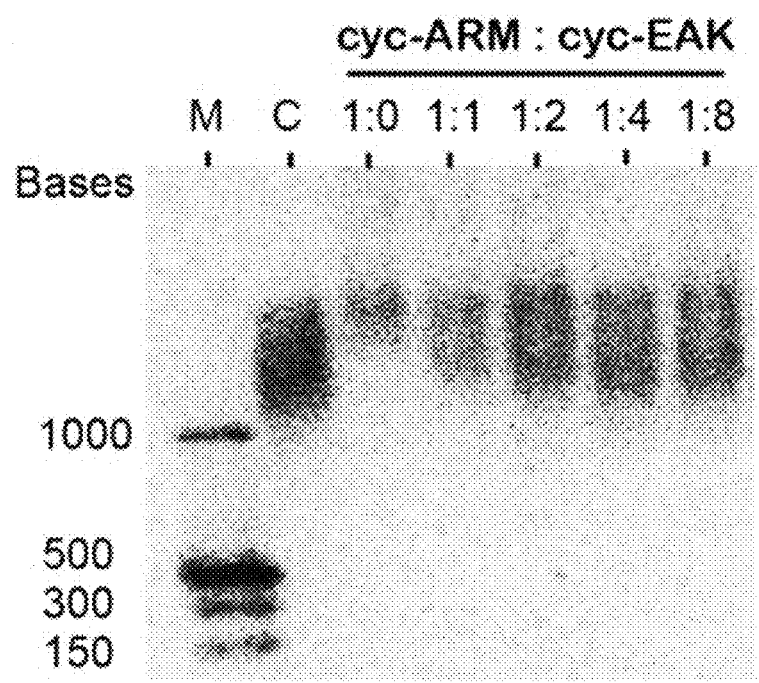
FIG. 18 illustrates EMSA results of the dependence of a co-assembly ratio on the inhibition of RRE:Rev interactions by the hetero-(A&E)-SPCH of the present disclosure (In FIG. 18, M denotes an RNA ladder)

Referring to FIG. 18, in competition experiments by EMSA, as the fraction of cyc-ARM decreased, the inhibitory ability of hetero-A&E-SPCH decreased.

The result shows that a relative rate of co-assembled peptides on the surface of inorganic SWCNTs is directly representative of a rate of peptides in a solution. Similar to the results of FIG. 12, lower parts of bands of the complexes first disappeared in the competition experiments.

To confirm whether the hybridization method can also be applied to peptides having different structural properties, a second self-assembling peptide of a linear type (lin-NES) including a Rev NES and a SWNT binding sequence was synthesized, and the lin-NES was labeled with fluorescein, which forms a fluorescence resonance energy transfer (FRET) pair with pyrene.

The second self-assembling peptide may include an NES and a self-assembly domain.

The NES may have an amino acid sequence of SEQ ID NO: 2 below, and the self-assembly domain may have an amino acid sequence of SEQ ID NO: 4 below.

<SEQ ID NO: 2>
CLPPLERLTR

<SEQ ID NO: 4>
KFEFKFEF

The second self-assembling peptide may be represented by Structural Formula 2 below, and may be a linear NES peptide (hereinafter, referred to as lin-NES).

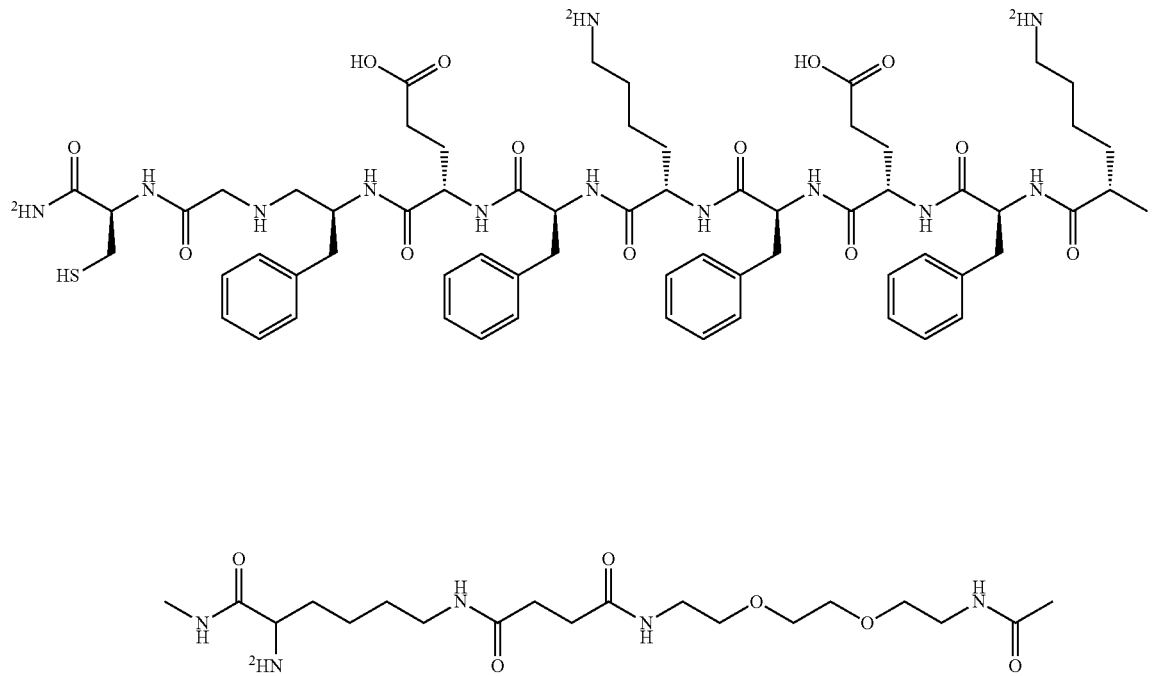

-continued

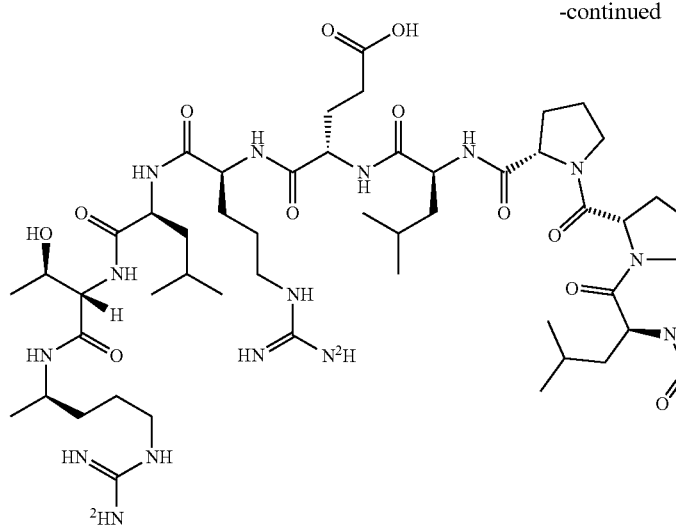
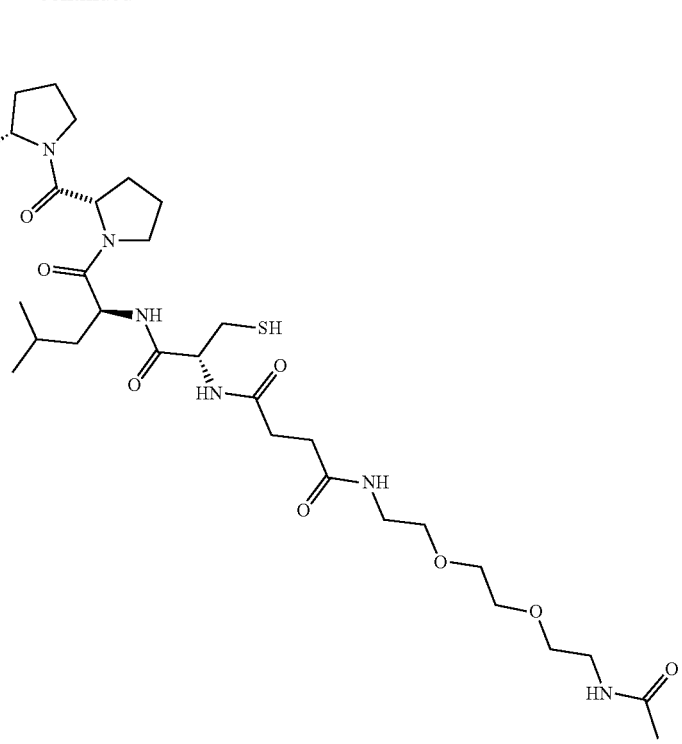

30

Figure 19:
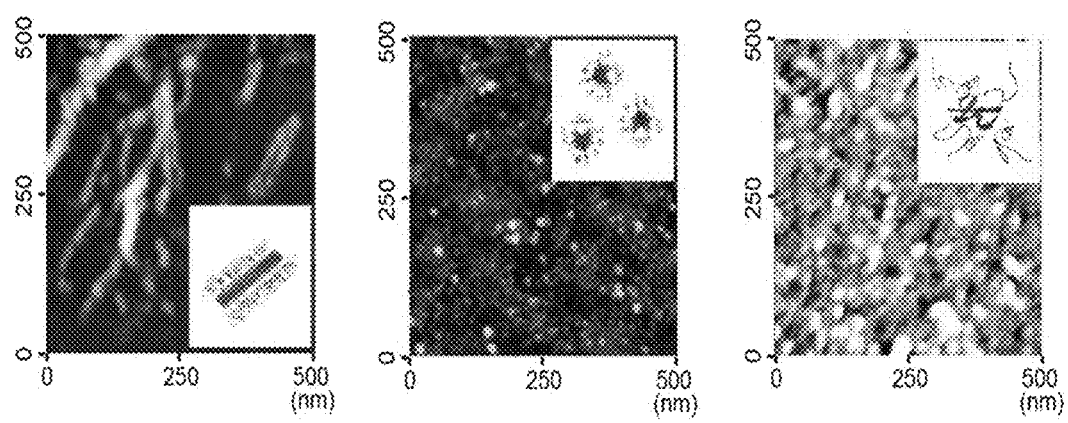
FIG. 19 illustrates atomic force microscopy (AFM) images of a lin-NES assembly (left), a cyc-ARM assembly (middle), and a co-assembled structure of the lin-NES and the cyc-ARM (right)

Referring to FIG. 19, morphologies of the lin-NES assembly (left image) and the cyc-ARM assembly (middle image) in the absence of SWCNTs were fibrillary and spherical, respectively. In the case of a bio-inorganic hybrid structure (hetero-(A&N)-SPCH) (right image) in which cyc-ARM and lin-NES are co-assembled, irregular aggregates are observed.

Figure 20:
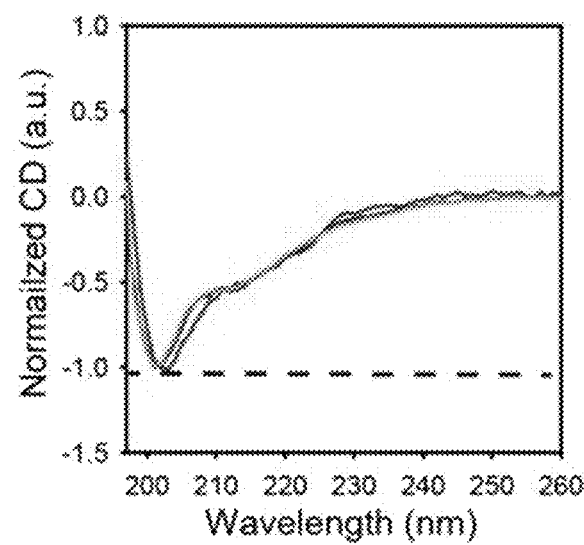
FIG. 20 illustrates normalized CD spectra of the lin-NES (blue), a co-assembled structure of the lin-NES and the cyc-NES (green), and the cyc-ARM (red) of the present disclosure.

Referring to FIG. 20, α-helix stabilization was not observed in cyc-ARM, lin-NES, and the co-assembled structure thereof.

Figure 21:
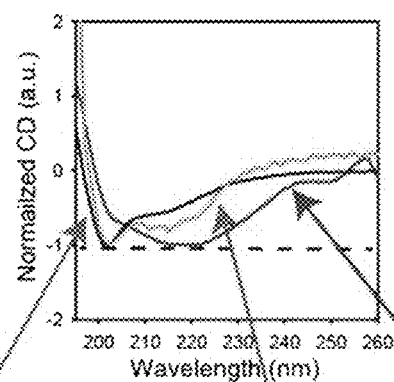
FIG. 21 illustrates normalized CD spectra of a homo-NES-SPCH (blue), a hetero-(A&N)-SPCH (green), and a homo-ARM-SPCH (red) of the present disclosure.
Figure 21:
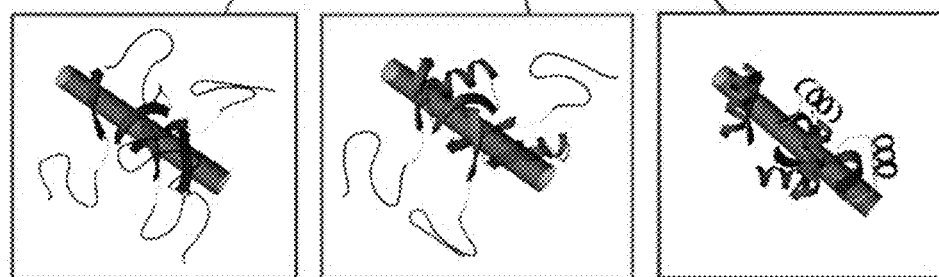

Referring to FIG. 21, in contrast to the results of FIG. 20, the CD spectra of the hetero-SPCH or hetero-(A&N)-SPCH assembly by the co-assembled structure exhibited a high degree of helix stabilization.

That is, the hybridization of SWCNTs may increase the helicity of peptides, which cannot be achieved by SWNT-free assemblies.

Figure 22:
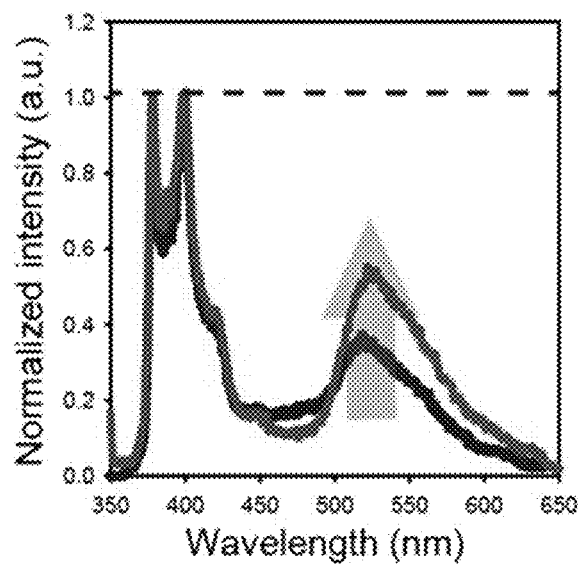
FIG. 22 illustrates fluorescence emission spectra of a co-assembled structure of the lin-NES and the cyc-ARM (blue), and the hetero-(A&N)-SPCH (red) of the present disclosure.

Referring to FIG. 22, hetero-(A&N)-SPCH exhibited a higher energy transfer efficiency than that of co-assembled peptides in the FRET assay.

That is, cyc-ARM and lin-NES may be more effectively mixed in sidewalls (red) of CNTs than in co-assembled irregular aggregates (blue). Thus, bioactive peptides with a variety of amino acid compositions, secondary structures and configurations may be stably positioned in hetero-SPCH via noncovalent hybridization.

Figure 23:
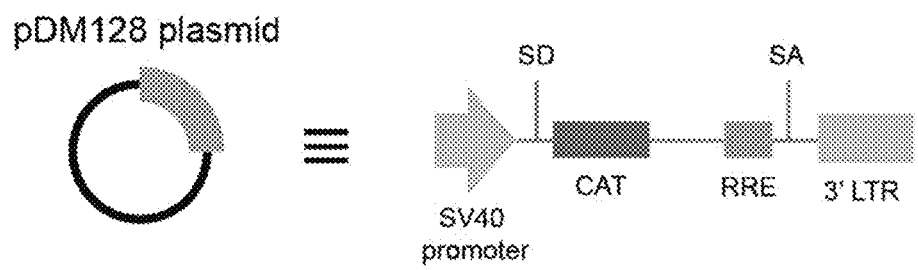
FIG. 23 is a schematic illustration of plasmid pDM128 of the present disclosure.

Lastly, multitarget-binding and inhibitory capabilities of hetero-SPCHs were examined. To evaluate the inhibition of Rev-mediated RRE export, a nucleocytoplasmic export assay based on plasmid pDM128 expressing RRE (see FIG. 23) was performed.

Figure 24:
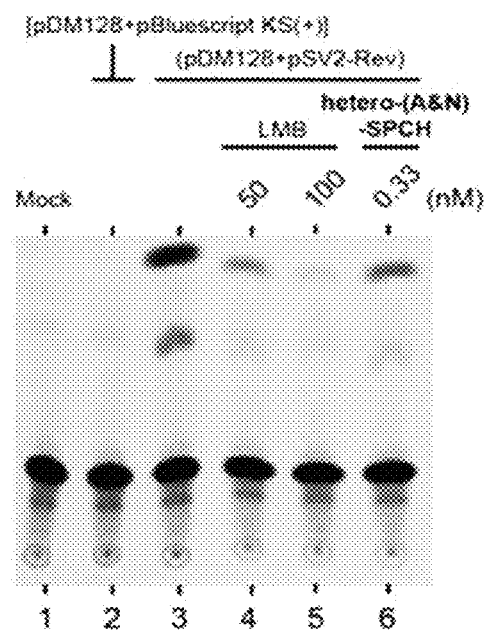
FIGS. 24 and 25 illustrate chloramphenicol acetyltransferase (CAT) assay results obtained by measuring the nucleocytoplasmic export of RRE RNA according to the present disclosure (The numbers above the gels of FIGS. 24 and 25 denote the concentrations of an LMB or an SPCH)
Figure 25:
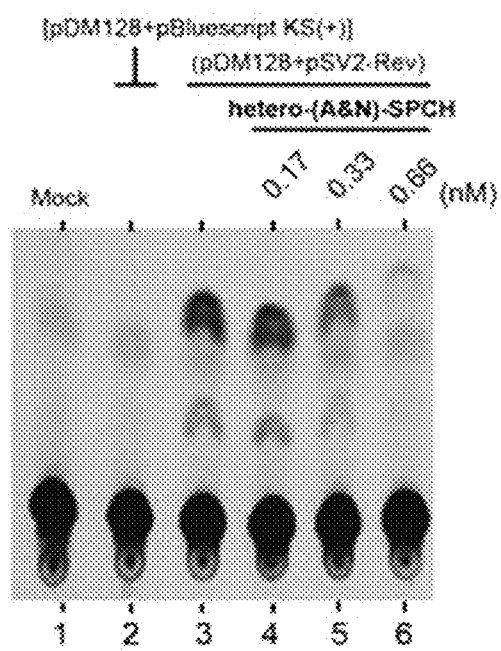
Figure 26:
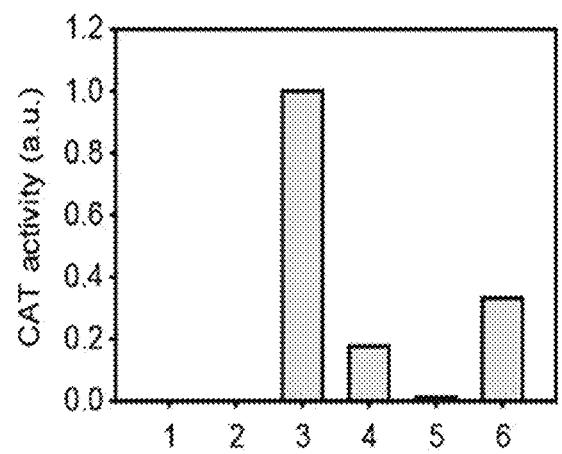
FIG. 26 is a graph showing densitometric analysis results of the CAT assay data of FIG. 24 according to the present disclosure.
Figure 27:
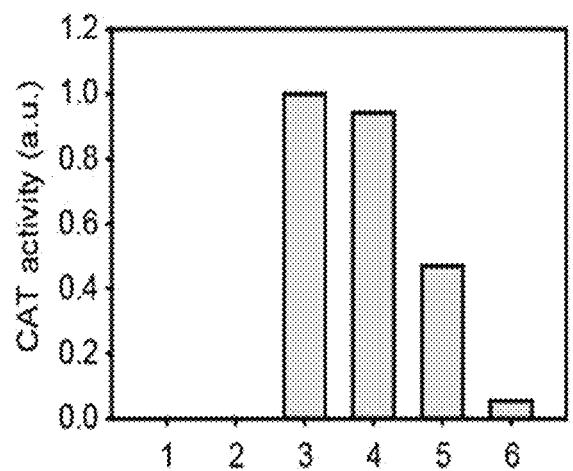
FIG. 27 is a graph showing densitometric analysis results of the CAT assay data of FIG. 25 according to the present disclosure.

Referring to FIG. 24, as shown in a chloramphenicol acetyltransferase (CAT) assay (lane 3), co-transfection of pDM128 with pSV2-Rev (Rev-expressing plasmid) in HeLa cells enables an effective nucleocytoplasmic export of RRE RNA. In contrast, negligible CAT activity was observed when the cells were co-transfected with pBluescript KS(+) (negative control plasmid) (lane 2).

In addition, to confirm whether nucleocytoplasmic export mediated by RRE: Rev: Crm1 interactions could be inhibited by peptide-CNT hybrids, the cells were treated with hetero-(A&N)-SPCHs.

Referring to FIGS. 24 to 27, the bio-inorganic hybrid inhibitor may reduce the expression of CAT genes in a concentration-dependent manner.

Figure 28:
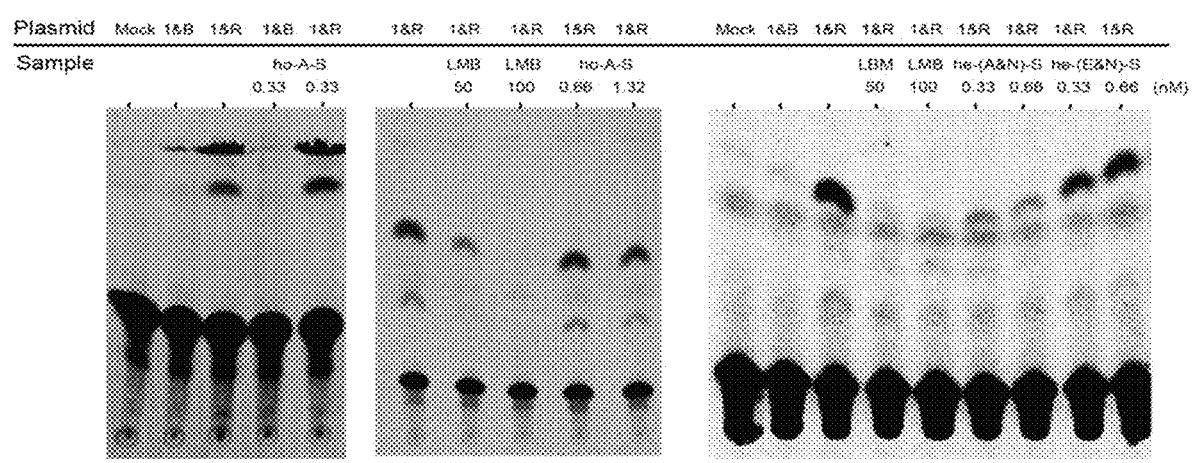
FIG. 28 illustrates CAT assay results by measurement of the nucleocytoplasmic export of RRE RNA according to the present disclosure (The numbers above the gels denote the concentrations of an LMB and an SPCH, 1&B is pDM128 & pBluscript KS(+), 1&R is pDM128 & pSV2-Rec, ho-A-S is homo-ARM-SPCH, he-(A&N)-S is hetero-(A&N)-SPCH, and he-(E&N)-S is hetero-(EAK&NESA)-SPCH).

Referring to FIG. 28, SPCHs targeting only a single interaction are unable to reduce the CAT activity when given at the same concentration. This indicates that the interactions must be simultaneously regulated to effectively inhibit multimolecular RNA-protein complexes.

Compared to leptomycin B (LMB), which is a well-known small-molecule inhibitor of the HIV-1 Rev-mediated pre-mRNA export from the nucleus, the hetero-(A&N)-SPCH shows an approximately 150-fold better performance as an inhibitor of the RNA-protein complexes. To completely inhibit the RRE export, 100 nM of LMB was required, while 0.66 nM of SPCHs was required.

The excellent inhibitory capability of the SPCHs is attributed to simultaneous multivalent display of peptide ligands directed towards two different targets and adaptable properties of the noncovalent assembly. Due to the adaptable properties, the assembly may be used to adjust the orientation and spacing of ligand units according to a particular 3D environment in target interfaces.

These results demonstrate that these types of hetero-SPCHs have potential as an effective therapeutic agent for diseases involving interactions among multiple pathogenic biomolecules.

The inventors of the present disclosure devised a novel strategy for regulating multiple biomolecular interactions using multivalent MTDLs. Instead of using small-molecule inhibitors, peptides, which are promising substances in the new drug development field, were displayed on a CNT scaffold having a longer length than that of general biomolecules.

The hybrid structures were prepared via a simple method using noncovalent interactions and showed excellent intracellular stability. With the multivalent display of peptide ligands, SPCHs showed an excellent target inhibitory capacity in the multitarget-directed assay.

The efficacy of drugs is limited by a low accumulation rate in decreased areas after administration, and thus the high therapeutic activity of a single drug is important in new drug development. That is, the excellent effects of multivalent supramolecular structures may provide new insight into MTDL-based treatment.

According to another embodiment of the present disclosure, a composition for inhibiting a multimolecular complex which includes the above-described hybrid structure is provided.

The composition may effectively inhibit multimolecular complexes that cannot be inhibited by existing drugs, due to size and multi-targeting characteristics.

The amount of the hybrid structure may range from about 0.0001 wt % to about 50 wt % with respect to the total weight of the composition, and the composition may further include one or more active ingredients exhibiting the same or similar functions.

The composition may be administered orally or parenterally. The composition may be systematically or locally administered, and the administration may include oral administration and parenteral administration. The composition may be formulated together with a suitable amount of a pharmaceutically acceptable vehicle or carrier to provide a suitable administration form.

The composition may further include a carrier, an excipient, and a diluent that are used for the preparation of a pharmaceutical composition. Examples of suitable carriers, excipients, and diluents include, but are not limited to, lactose, dextrose, sucrose, sorbitol, mannitol, xylitol, erythritol, maltitol, starch, acacia rubber, alginate, gelatin, calcium phosphate, calcium silicate. cellulose, methyl cellulose, microcrystalline cellulose, polyvinylpyrrolidone, water, methyl hydroxybenzoate, propyl hydroxybenzoate, talc, magnesium stearate, and mineral oil.

The composition may be formulated in the form of oral preparations such as powder, granules, tablets, capsules, suspensions, emulsions, syrups, aerosols, and the like, preparations for external application, suppositories, and sterile injection solutions.

Examples of solid preparations for oral administration include tablets, pills, powder, granules, capsules, and the like, and these solid preparations may be formulated by mixing the compound and fractions thereof with one or more excipients, for example, starch, calcium carbonate, sucrose, lactose, gelatin, or the like. In addition, a lubricant such as magnesium stearate or talc may be used in addition to the above-described excipient.

Examples of liquid preparations for oral administration include suspensions, liquids for internal use, emulsions, syrups, and the like, and these liquid preparations may include, in addition to simple commonly used diluents such as water and liquid paraffin, various types of excipients, for example, a wetting agent, a sweetener, a flavoring agent, a preservative, and the like.

Preparations for parenteral administration include an aqueous sterile solution, a non-aqueous solvent, a suspension, an emulsion, a freeze-dried preparation, and a suppository. Non-limiting examples of the non-aqueous solvent and the suspension include propylene glycol, polyethylene glycol, a vegetable oil such as olive oil, and an injectable ester such as ethyl oleate. Examples of suppository bases include Witepsol, Macrogol, Tween 61, cacao butter, laurin, glycerogelatin, and the like.

The pharmaceutical composition may be administered to a subject in a pharmaceutically effective amount. The term "pharmaceutically effective amount" as used herein refers to an amount sufficient to treat diseases at a reasonable benefit/risk ratio applicable to medical treatment, and an effective dosage level may be determined according to factors including type of diseases of patients, the severity of disease, the activity of drugs, sensitivity to drugs, administration time, administration route, excretion rate, treatment periods, and simultaneously used drugs, and factors well known in other medical fields.

The pharmaceutical composition may be administered as an individual therapeutic agent or in combination with other therapeutic agents, may be administered sequentially or simultaneously in combination with an existing therapeutic agent, and may be administered in a single dose or multiple doses. The pharmaceutical composition may be administered in an amount that allows the maximum effects to be obtained in a minimum amount without side effects in consideration of all the above-described factors, which may be easily determined by those of ordinary skill in the art.

Hereinafter, the present disclosure will be described in further detail with reference to the following examples. However, it is obvious that these examples are not intended to limit the scope of the present disclosure.

Experimental Examples

Tissue Culture and Intracellular Experiment

To microscopically observe the intracellular delivery of a peptide/CNT hybrid (SPCH) structure, $1\times10^4$ HeLa cells were distributed into an 8-well Lab-Tek II chamber cover glass system (Nunc) in Dulbecco's modified Eagle's medium (DMEM) supplemented with 10% fetal bovine serum (FBS) and 1% pen/strep and incubated under 5% $CO_2$ at 37° C.

The incubated cells were washed with Dulbecco's phophate-buffered saline (DPBS), and then treated with the hybrid structure for 4 hours. Subsequently, the sample solution was removed, and the cells were further cultured for 1 hour.

The cultured cells were visualized using a confocal microscope (LSM710, Carl Zeiss, Germany). To perform a FRAP assay, small areas of the cells were photobleached with pyrene fluorescence, and observed for 300 seconds at an interval of 1 image per approximately 2 seconds.

EMSA with Full-Length RRE RNA

EMSAs were performed in a binding buffer having a composition of 10 mM HEPES-KOH (pH 7.5), 100 mM KCl, 1 mM $MgCl_2$, and 10% glycerol. To form a complex, 7 μL of a sample solution was mixed with 3 μL of a 100 nM full-length RRE RNA solution.

The reaction product was incubated at room temperature for 1 hour or more, and transferred to a 1.2% agarose (1×TBE) gel. Electrophoresis was followed at 150 V and room temperature for about 45 minutes, and RNA was stained with a SYBR Green II RNA gel staining reagent to be visualized.

Chloramphenicol Acetyltransferase (CAT) Assay

HeLa cells were incubated under 5% $CO_2$ at 37° C. in DMEM supplemented with 10% FBS and 1% pen/strep. $4\times10^4$ of the incubated cells were distributed into a 48-well plate, and then incubated under 5% $CO_2$ at 37° C. overnight. Subsequently, the resulting cells were washed with DPBS, and then a plasmid (total 250 ng; pDM128, pBluescript II KS (+), pSV2-Rev) complexed with 0.7 μL of a jetPEI DNA transfection reagent was added to each well.

After transfection for 6 hours, the cells were washed with DPBS and cultured in DMEM/FBS for 42 hours. Subsequently, the cells were washed with DPBS and incubated at 37° C. for 10 minutes, and then 200 μL of a cell lysis buffer (Promega, USA) was added thereto.

The resulting cells were collected and centrifuged at a maximum speed of 16,110×g at 4° C. for 10 minutes. The supernatant was collected, incubated at 65° C. for 10 minutes, and centrifuged at a maximum speed of 16,110×g in a tabletop centrifuge, and then 200 μL of a cell lysis buffer (Promega, USA) was further added thereto.

The samples were normalized with the concentrations of proteins measured by a BCA assay (BCA protein assay kit; Pierce, USA). Each sample was mixed with a reaction mixture [1M Tris-Cl, pH 7.8, 3.5 mg/mL acetyl-CoA, and 1 μL of 14C-radiolabeled chloramphenicol (PerkinElmer)], and cultured at 37° C. for 2 hours.

Subsequently, 1 mL of ethyl acetate was added to the resulting mixture, followed by vortexing for 10 minutes. The resulting mixture was centrifuged at 22,000×g for 5 minutes, and 800 μL of a supernatant organic phase was collected and concentrated to 100 μL or less by vaporization.

The product was isolated by thin-layer chromatography (TLC) (95% chloroform, 5% methanol), and the TLC sheet was exposed to a phosphor-imaging plate for 12 hours. The image was visualized by Typhoon FLA-700 PhosphorImager (GE Healthcare Life Sciences, USA), and then processed using Multigauge software.

Experimental Methods

Synthesis of Peptides

Peptides were synthesized in Rink Amide MBHA resin LL (Novabiochem) via Fmoc protocols using the Tribute peptide synthesizer (Protein Technologies, USA). Amino acids except for Cys (Mnt) and Lys (Dde) were protected using a general method, and each of acid-labile methoxytrityl (Mnt) and N-[1-(4,4-dimethyl-2,6-dioxocyclohex-1-ylidene)ethyl](Dde) groups was used.

During side chain-to-tail cyclization, bromoacetic acid was first bound to the N-terminal portion of a resin-bound peptide.

Before the resin was added, for carboxyl activation, a mixture of 28 mg (200 μmol) of bromoacetic acid and 15.5 μL (100 μmol) of N,N'-diisopropylcarbodiimide was cultured in n-methyl-2-pyrrolidinone (NMP) for 10 minutes.

After the mixture was added to the resin, the resulting mixture was shake-cultured at room temperature for 10 minutes. For orthogonal deprotection of the Mnt groups from cysteine, the resin was treated with 1% trifluoroacetic acid (TFA) in dichloromethane (DCM) for several hours (1 min×~7).

Intramolecular cyclization was carried out in 3 μL of 1% diisopropylethylamine (DIPEA) in NMP under room-temperature shaking conditions. Deprotection of Dde from Lys (Dde) was carried out in 2% hydrazine of dimethylformamide (DMF).

Subsequently, fluorophore binding was carried out according to standard Fmoc protocols. To perform Dapoxyl fluorophore labeling, leucine residues of the tail segment were substituted with Lys (Dde), and Dapoxyl™ succinimidyl ester was conjugated with the orthogonally deprotected lysine residues.

For final deprotection and isolation from the resin, the resin-bound peptide was treated with a cleavage cocktail prepared by mixing TFA, triisopropylsilane (TIS), and water in a mixing ratio of 95:2.5:2.5 for 3 hours, and triturated with tert-butyl methyl ester.

The peptide was purified by reversed-phase HPLC (water/acetonitrile with 0.1% TFA). The molecular weight of the peptide was measured by a matrix-assisted laser desorption/ionization time-of-flight (MALDI-TOF) mass spectrometer (Microflex LRF20, Brunker).

α-Cyano-4-hydroxycinnamic (CHCA) was used as a matrix. The concentration of the peptide was measured in water/acetonitrile (1:1) by spectrophotometry using the molar extinction coefficient of pyrene (8790 $cm^{-1}$) at 350 nm and the molar extinction coefficient of fluorescein (428 $cm^{-1}$) at 495 nm.

Measurement Example (1) Circular Dichroism (CD) Measurement

CD was measured using a Chriscan™ Circular Dichroism spectrometer (Applied Photophysics, USA) equipped with a Peltier temperature controller.

CD spectra of the peptides were recorded at 190 nm to 260 nm using a cuvette having a path length of 1 mm.

(2) Atomic Force Microscopy (AFM) Analysis

For AFM analysis, about 1 μl of the sample was precipitated into freshly isolated mica. After the sample was completely dried, the residual salt of distilled water was removed under the steam of argon gas.

Images were acquired in a tapping mode using a Nanoscope IV instrument (Digital Instruments). AFM scans were obtained at a set value ranging from 0.8 V to 1 V, and the scan rate was 1 Hz to 2 Hz.

(3) Transmission Electron Microscopy (TEM) Analysis

1 μl of the sample was completely dried on a carbon-coated copper lattice. Subsequently, to remove salt crystals, 1 μl of water was added for 1 minute and then removed using filter paper.

The specimens were observed at 120 kV using a JEOL-JEM 2010 instrument. Then, 2 μl of 2% (w/v) uranyl acetate was added for 1 minute, and then the excess solution was removed using filter paper.

(4) Fluorescence Analysis (Leakage Experiment)

Steady state fluorescence spectra were recorded from a quartz cuvette having a path length of 1 cm using a PerkinElmer LS-55 fluorescence spectrophotometer.

To measure fluorescence from pyrene and rhodamine B, samples were excited at 340 nm and 550 nm, respectively. An excitation-emission slit with a bandpass of 5 nm was used for the measurement.

(5) Full-Length RRE RNA: Plasmids Construction and In Vitro Transcription

The plasmid pDM128 containing a 240-nt RRE sequence (5122-5361) was amplified by a polymerase chain reaction (PCR). The forward primer was CGAGAGCTCGCTATGT-TCCTTGGGTT <SEQ ID NO: 6> containing a Sac I site (GAGCTC).

The reverse primer was CGTGGTACCATCCCTAG-GAGCTGTTG <SEQ ID NO: 7> containing a Kpn I site (GGTACC). To increase the cleavage efficiency of restriction enzymes, three bases were added to the 5'-terminal of each primer.

A 236-nt RRE sequence (5126-5361 from pDM128) was isolated from the plasmid pDM128 by PCR using the TOYOBO Taq polymerase HS mix (DTM-101) at a heat treatment temperature of 61° C. to 62° C. This resulted in 245-bp dsDNA.

The obtained PCR fragment was purified by electrophoresis on 1.5% agarose gel and double cleaved with Sac I and Kpn I. The 254-bp fragment was ligated to the Sac I-Kpn I sites of pBluescript II KS(+). Transformed bacteria were cultured on an agar plate containing 50 µg/mL of ampicillin.

The RRE sequences were confirmed by sequencing of T7 promoter primers (Macrogen, Korea). The replication plasmid pBlue-RRE (5-240) was linearized by Acc65 I cleavage to yield a 5' overhang.

In vitro transcription was performed using an Ambion MEGAscript™ T7 Kit (AM1333). The transcript RNA was purified by 6% urea PAGE, and recovered by Elutrap, resulting in ethanol precipitation. The 253-nt transcript RNA sequence is as follows (the underlined part is a 236-nt RRE RNA sequence):

5'-GGGCGAAUUGGAGCUC<u>GCUAUGUUCCUUGGGUUCUUGGGGAGCAGCAG</u>

<u>GAAGCACUAUGGGCGCAGUGUCAUUGACGCUGACGGUACAGGCCAGACAA</u>

<u>UUAUUGUCUGGUAUAGUGCAACAGCAGAACAAUUUGCUGAGGGCUAUUGA</u>

<u>GGCGCAACAACAUCUGUUGCAACUCACAGUCUGGGGCAUCAAGCAGCUCC</u>

<u>AGGCAAGAGUCCUGGCUGUGGAAAGAUACCUAAGGGAUCAACAGCUCCUA</u>

<u>GGGAUG</u>-3'

According to the present disclosure, an inorganic material having a much larger size than that of an inhibitor is introduced as a backbone, and thus an effect of binding a great number of heterogeneous inhibitors to a single material via self-assembly based on the inorganic material can be obtained.

In addition, a bio-inorganic hybrid structure enables multivalent interactions exhibiting much higher binding than general interactions and can also exhibit a high efficiency in binding multiple pathogenic biomolecules to a single therapeutic material.

In addition, the bio-inorganic hybrid structure uses a peptide more suitable for the inhibition of bio-binding than small chemical molecules, and thus can provide a higher therapeutic effect and higher biocompatibility.

The foregoing description of the present disclosure is provided for illustrative purposes only, and it will be understood by those of ordinary skill in the art to which the present disclosure pertains that the invention may be easily modified in many different forms without departing from the spirit or essential characteristics of the present disclosure. It is therefore to be understood that the above-described embodiments are illustrative in all aspects and not restrictive. For example, each component described as being in a single form may be embodied in a distributed form, and, in the same manner, components described as being in a distributed form may be embodied in an integrated form.

The scope of the present disclosure is defined by the following claims, and all modifications or variations derived from the meaning, scope, and equivalents of the claims should be construed as falling within the scope of the present disclosure.

What is claimed is:

1. A hybrid structure comprising:

carbon nanotubes; and a first self-assembling peptide and a second self-assembling peptide, both bound to a surface of the carbon nanotubes and each independently binding different target molecules;

wherein the first and second self-assembling peptides each comprise a self-assembly domain;

and wherein:

the first self-assembling peptide comprises an arginine rich motif (ARM) comprising the amino acid sequence of SEQ ID NO: 1 (TRQARRNRRRRWRR);

the second self-assembling peptide comprises a nuclear export signal (NES) comprising the amino acid sequence of SEQ ID NO: 2 (CLPPLERLTR); and the self-assembly domain comprises the amino acid sequence of SEQ ID NO: 4 (KFEFKFEF).

2. A composition for inhibiting a multimolecular complex, the composition comprising the hybrid structure according to claim 1.

* * * * *